Figure 1A:
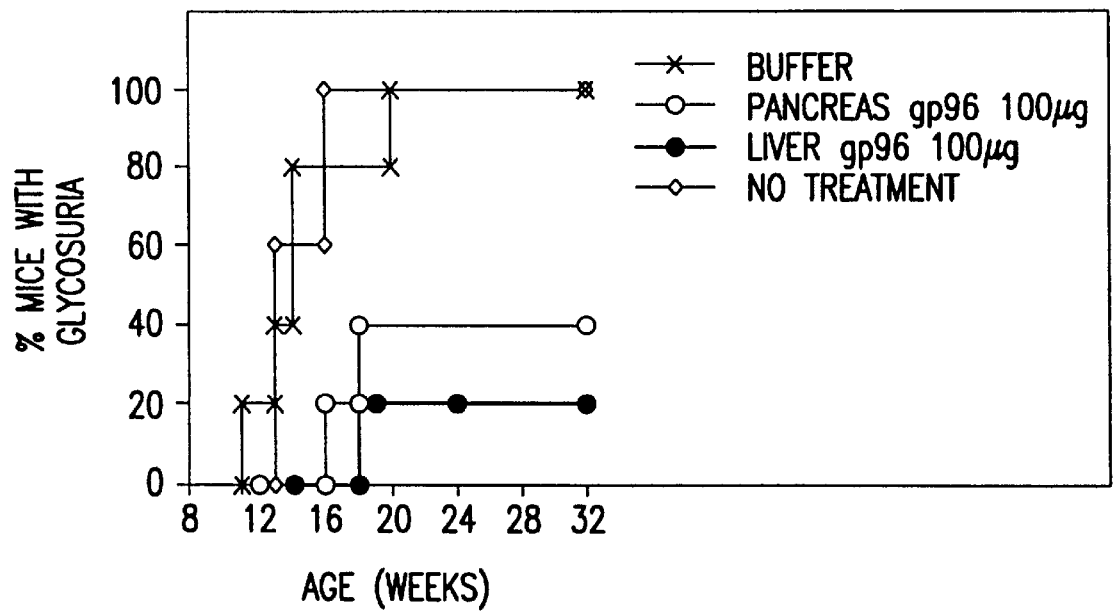

United States Patent [19]
Srivastava et al.

[11] Patent Number: 6,007,821
[45] Date of Patent: Dec. 28, 1999

[54] METHOD AND COMPOSITIONS FOR THE TREATMENT OF AUTOIMMUNE DISEASE USING HEAT SHOCK PROTEINS

[75] Inventors: Pramod K. Srivastava, Avon, Conn.; Rajiv Y. Chandawarkar, Akron, Ohio

[73] Assignee: Fordham University, Bronx, N.Y.

[21] Appl. No.: 08/951,789

[22] Filed: Oct. 16, 1997

[51] Int. Cl.$^6$ .................. A61K 39/00; A61K 39/385; A01N 37/18; C07K 14/435
[52] U.S. Cl. ................ 424/193.1; 424/810; 424/184.1; 514/2; 514/825; 514/866; 514/903; 530/350; 530/806; 530/827; 530/868
[58] Field of Search .................. 424/193.1, 810, 424/184.1; 514/2, 866, 903, 825; 530/350, 806, 827, 868

[56] References Cited

U.S. PATENT DOCUMENTS

| | | |
|---|---|---|
| 5,268,170 | 12/1993 | Van Eden et al. |
| 5,354,691 | 10/1994 | Van Eden et al. |
| 5,578,303 | 11/1996 | Cohen et al. |
| 5,750,119 | 5/1998 | Srivastava . |
| 5,830,464 | 11/1998 | Srivastava . |
| 5,837,251 | 11/1998 | Srivastava . |

FOREIGN PATENT DOCUMENTS

| | | |
|---|---|---|
| 0 764 273 B1 | 8/1995 | European Pat. Off. |
| WO 89/12455 | 12/1989 | WIPO . |
| WO 94/29459 | 12/1994 | WIPO . |
| WO 95/15338 | 6/1995 | WIPO . |
| WO 95/15339 | 6/1995 | WIPO . |
| WO 95/33997 | 12/1995 | WIPO . |
| WO 98/19167 | 5/1998 | WIPO . |
| WO 98/23735 | 6/1998 | WIPO . |

OTHER PUBLICATIONS

Tisch, R and McDevitt, HO. Proc. Nat. Acad. Sci. (USA) 91:437–438, Jan. 1994.
Tamura, Y. et al. Science 278:117–120. Oct. 1997.
Nieland, TJF et al. Proc. Nat. Acad. Sci. (USA) 93:6135–6139. Jun. 1996.
Suto, R et al. Science 269:1585–1588, Sep. 1995.
Adamec et al., 1996, "Development of the Surgical Technique and Tactics of Combined Pancreas and Kidney Transplantation With Respect to the Incidence of Surgical Complications", *Transplantation Proceedings* 28–6:3347.
Akhtar et al., 1995, "CD4$^+\beta$ islet cell–reactive T cell clones that supress autoimmune diabetes in nonobese diabetic mice", *J. Exp. Med.* 182:87–97.
Bardwell et al., 1984, "Major heat shock gene of Drosophila and the *Escherichia coli* heat inducible dnaK gene are homologous", *Proc. Natl. Acad. Sci.* 81:848–852.
Blachere et al., 1993, "Heat Shock Protein Vaccines Against Cancer", *J. of Immunotherapy* 14:352–356.
Birk et al., 1993, "T–Cell autoimmunity in type 1 diabetes mellitus", *Current Opinion in Immunology* 5:903–909.
Birk et al., 1996, "NOD Mouse Diabetes: The Ubiquitous Mouse Hsp60 is a β–Cell Target Antigen of Autoimmune T Cells", *J. of Autoimmunity* 9:159–166.
Birk et al., 1996, "A role of Hsp60 in autoimmune diabetes: Analysis in a transgenic model", *P.N.A.S.* 93:1032–1037.
Bockova et al., 1997, "Treatment of NOD Diabetes with a Novel Peptide of the Hsp60 Molecule Induces Th2–type Antibodies", *J. of Autoimmunity* 10:323–329.

(List continued on next page.)

*Primary Examiner*—David Saunders
*Assistant Examiner*—F. Pierre VanderVegt
*Attorney, Agent, or Firm*—Pennie & Edmonds LLP

[57] ABSTRACT

The invention relates to methods and compositions for the treatment of autoimmune disease. Specifically, compositions comprising heat shock proteins, including gp96, hsp90, and hsp70, are disclosed. Immunotherapeutic methods for administering the hsp-containing compositions are disclosed. Furthermore, methods for preventing rejection of organs transplanted to treat autoimmune disease are disclosed. The disclosed methods are useful for treating a variety of autoimmune diseases, including insulin dependent diabetes mellitus.

40 Claims, 7 Drawing Sheets

OTHER PUBLICATIONS

Bohme et al., 1990, "MHC–linked protection from diabetes dissociated from clonal delection of T cells", *Science* 249:293–295.

Boitard et al., 1989, "T cell–mediated inhibition of the transfer of autoimmune diabetes in NOD mice", *J. Exp. Med.* 169:1669–1680.

F.C. Brunicardi, 1996, "Clinical islet transplantation: A consortium model", *Transplantation Proceedings* 28:2138–2140.

Castaño and Eisenbarth, 1990, "Type–I diabetes: A chronic autoimmune disease of human, mouse, and rat", *Annu. Rev. Immunol.* 8:647–679.

Chosich and Harrison, 1993, "Suppression of diabetes mellitus in the non–obese diabetic (NOD) mouse by an autoreactive (anti–I–A$^{g7}$) islet–derived CD4$^+$ T–cell line", *Diabetologia* 36:716–721.

Cohen R.C. et al., 1991, "Autoimmunity to the Chaperonins in the Pathogenesis of Arthritis and Diabetes" *Ann. Rev. Immunol.* 9:567–589.

Cohen R.C., 1992, "Immunologically Specific Treatment of Spontaneous Insulin–dependant Diabetes Mellitus of NOD Mice" *J. of Autoimmunity* 5:227–230 (Supplement A).

Cohen R.C., 1997, Short Analytical Review; The Th1–Th2 Dichotomy, hsp60 Autoimmunity, and Type 1 Diabetes *Clin. Immuno. and Immunopathology* 84–2:103–106.

Cohen R.C. et al., 1996, "Immunity to 60kDa heat shock protein in autoimmune diabetes" *Diab. Nutr. Metab.* 9:229–232.

Cohen R.C. et al., 1992, "Autoimmunity to Hsp65 and the Immunologic Paradigm*", *Advances In Internal Medicine* 37:295–311.

E.A. Craig, 1993, "Chaperones: Helpers along the pathways to protein folding", *Science* 260:1902–1903.

Demotz et al., 1989, "Characterization of a naturally processed MHC class II–restricted T–cell determinant of hen egg lysozyme", *Nature* 342:682–684.

Elias and Cohen, 1994, "Peptide therapy for diabetes in NOD mice", *Lancet* 343:704–706.

Elias et al.,1994, "Autoimmune Diabetes Induced by the β–Cell Toxin STZ; Immunity to the 60–kDa Heat Shock Protein and to Insulin", *Diabetes* 43:992–998.

Elias et al., 1990, "Induction and therapy of autoimmune diabetes in the non–obese diabetic (NOD/Lt) mouse by a 65–kDA heat shock protein", *Proc. Natl. Acad. Sci.* 87:1576–1580.

Elias et al., 1991, "Vaccination against autoimmune mouse diabetes with a T–cell epitope of the human 65–k–Da heat shock protein", *Proc. Natl. Acad. Sci.* 88:3088–3091.

Elias et al., 1995, "Induction of diabetes in standard mice by immunization with the p277 peptide of a 60–kDa heat shock protein", *Eur. J. Immunol.* 25:2851–2857.

Elias and Cohen, 1995, "Treatment of autoimmune diabetes and insulitis in NOD mice with heat shock portein 60 peptide p277", *Diabetes* 44:1132–1138.

Elias et al., 1996, "The hsp60 Peptide p227 Arrests the Autoimmune Diabetes Induced by the Toxin Streptozotocin" *Diabetes* 45:1168–1172.

Elliott et al., 1990, "Naturally processed peptides", *Nature* 348:195–197.

Falk et al., 1990, "Cellular peptide composition governed by major histocompatibility complex class I molecules", *Nature* 348:248–251.

Falk et al., 1991, "Allele–specific motifs revealed by sequencing of self–peptides eluted from MHC molecules", *Nature* 351:290–296.

Feige et al., 1994, "A Constitutive 65 Kda Chondrocyte Protein as a Target Antigen in Adjuvant Arthritis in Lewis Rats"*Autoimmunity* 17:233–239.

Feige et al., 1996, "Infection, autoimmunity and autoimmune disease" *Stress Inducible Cellular Responses* eds. Birkhauser Velag Basel, Switzerland.

Gething and Sambrook, 1992, "Protein folding in the cell", *Nature* 355:33–45.

Hamaguchi and Leiter, 1990, "Comparison of cytokine effects on mouse prancreatic α–cell and β–cell lines", *Diabetes* 39:415–425.

Hamano et al., 1996, "Pancreas transplantation using non–suture cuff technique in the neck", *Kobe J. Med. Sci.* 42:93–104.

Haskins and McDuffie, 1990, "Acceleration of diabetes in young NOD mice with a CD4$^+$ islet–specific T cell clone", *Science* 249:1433–1436.

Heufelder et al., 1992, "Cell Surface Localization of a 72 Kilodalton Heat Shock Protein in Retroocular Fibroblasts from Patients with Graves Ophthalmopathy" *J. of Clin. Endocrino. And Metabolism* 74–4:732–736.

Hickey et al., 1989, "Sequence and regulation of a gene encoding a human 89–kilodalton heat shock protein", *Molecular and Cellular Biology* 9:2615–2626.

Hunt and Morimoto, 1985, "Conserved features of eukaryotic hsp70 genes revealed by comparison with the nucleotide sequence of human hsp70", *Proc. Natl. Acad. Sci.* 82:6455–6459.

Jindal et al., 1989, "Primary structure of a human mitochondrial protein homologous to the bacterial and plant chaperonins and to the 65–kilodalton mycobacterial antigen", *Molecular and Cellular Biology* 9:2279–2283.

Jones David.B. et al., 1993, "Sequence homologies between hsp60 and autoantigens" *Immunology Today* 14–3:115–118.

Kaufman et al., 1993, "Spontaneous loss of T–cell tolerance to glutamic acid decarboxylase in murine insulin–dependent diabetes", *Nature* 366:69–71.

Kendall et al., 1996, "Pancreas and islet transplantation in humans", *Diabetes & Metabolism* (*Paris*) 22:157–163.

Kinkhabwala et al., 1996, "The role of whole organ pancreas transplantation in the treatment of type I diabetes", *The American Journal of Surgery* 171:516–520.

Könen–Waisman et al., 1995, "Self and Foreign 60–Kilodalton Heat Shock Protein T Cell Epitope Peptides Serve as Immunogenic Carriers for a T Cell–Independent Sugar Antigen" *J. of Immunology* 154:5977–5985.

Lai et al., 1984, "Quantitation and intracellular localization of the 85K heat shock protein by using monoclonal and polyclonal antibodies", *Molecular and Cellular Biology* 4:2802–2810.

Larsen and Stratta, 1996, "Pancreas transplantation: A treatment option for insulin–dependent diabetes mellitus", *Diabetes & Metabolism* (*Paris*) 22:139–146.

Lèvy et al., 1991, "ATP is required for in vitro assembly of MHC class I antigens but not for transfer of peptides across the ER membrane", *Cell* 67:265–274.

Li and Srivastava, 1993, "Tumor rejection antigen gp96/grp94 is an ATPase: Implications for protein folding and antigen presentation", *The EMBO Journal* 12:3143–3151.

Lider et al., 1988, "Anti–idiotypic network induced by T cell vaccination against experimental autoimmune encephalomyelitis", *Science* 239:181–183.

Lindquist and Craig, 1988, "The heat–shock proteins", *Annu. Rev. Genet.* 22:631–677.

Lo et al., 1989, "Tolerance in transgenic mice expressing class II major histocopatibility complex on pancreatic acinar cells", *J. Exp. Med.* 170:87–104.

Maki et al., 1990, "Human homologue of murine tumor rejection antigen gp96: 5'–Regulatory and coding regions and relationship to stress–induced proteins", *Proc. Natl. Acad. Sci.* 87:5658–5662.

Makino S. et al., 1981, "Establishment of the Nonobese–diabetic (NOD) mouse" *Current topics in clinical and experimental aspects of diabetes mellitus;* eds. pp.25–32 ( Elsevier: Amsterdam).

Misaki et al., 1994, "Induction in vitro of 72–kD heat shock protein in a continuous culture of rat thyroid cells, FRTL5" *Clin. Exp. Immunol.* 98:234–239.

Miyazaki et al., 1990, "Direct evidence for the contribution of the unique I-A$^{NOD}$ to the development of insulitis in non–obese diabetic mice",*Nature* 345:722–726.

Mor et al., 1992, "T Cells in the Lesion of Experimental Autoimmune Encephalomyelitis" *J. Clin. Invest.* 90:2447–2455.

Nakano et al., 1991, "T cell receptor V gene usage of islet β cell–reactive T cells is not restricted in non–obese diabetic mice", *J. Exp. Med.* 173:1091–1097.

Nishimoto et al., 1987, "Prevention of autoimmune insulitis by expression of I–E molecules in NOD mice", *Nature* 328:432–434.

Pankewycz et al., 1992, "A protective NOD islet–infiltrating CD8$^+$ T cell clone, I.S. 2.15, has in vitro immunosuppressive properties", *Eur. J. Immunol.* 22:2017–2023.

Prakken et al., 1996, "Autoreactivity to Human Heat Shock Protein 60 Predicts Disease Remission in Oligoarticular Juvenile Rheumatoid Arthritis" *Arthritis & Rheumatism* 39–11:1826–1832.

Rapoport et al., 1993, "Interleukin 4 reverses T cell proliferative unresponsiveness and prevents the onset of diabetes in nonobese diabetic mice", *J. Exp. Med.* 178:87–99.

Reich et al., 1989, "Prevention of diabetes in NOD mice by injection of autoreactive T–lymphocytes", *Diabetes* 38:1647–1651.

Reich, et al., 1989, "An explanation for the protective effect of the MHC class II I–E molecule in murine diabetes", *Nature* 341:326–328.

Rötzschke et al., 1990, "Isolation and analysis of naturally processed viral peptides as recognized by cytotoxic T cells", *Nature* 348:252–254.

Rötzschke et al., 1990, "Characterization of naturally occurring minor histocompatibility peptides including H–4 and H–Y", *Science* 249:283–287.

Salvetti et al., 1992, "T–Lymphocyte Reactivity to the Recombinant Mycobacterial 65– and 70–kDa Heat Shock Proteins in Multiple Sclerosis" *J. of Autoimmunity* 5:691–702.

Salvetti et al., 1996, "The immune response to mycobacterial 70–kDa heat shock proteins frequently involves autoreactive T cells and is quantitatively disregulated in Multiple Sclerosis" *J. of Neuroimmunology* 65:143–153.

Serreze et al., 1988, "Defective activation of T suppressor cell function in nonobese diabetic mice", *The Journal of Immunology* 140:3801–3807.

Serreze et al., 1993, "Defects in the differentiation and function of antigen presenting cells in NOD/Lt Mice[1]", *The Journal of Immunology* 150:2534–2543.

Serreze et al., 1993, "Hematopoietic stem–cell defects underlying abnormal macrophage development and maturation in NOD/Lt mice: Defective regulation of cytokine receptors and protein kinase C", *Proc. Natl. Acad. Sci.* 90:9625–9629.

Shinnick et al., 1987, "The etiologic agents of leprosy and tuberculosis share an immunoreactive protein antigen with the vaccine strain *Mycobacterium bovis* BCG", *Infection and Immunity* 55:1932–1935.

Singer et al., 1993, "An Ab$^d$ transgene prevents diabetes in nonobese diabetic mice by inducing regulatory T cells", *Proc. Natl. Acad. Sci.* 90:9566–9570.

Slattery et al., 1990, "Prevention of diabetes in non–obese diabetic I–A$^k$ transgenic mice", *Nature* 345:724–726.

Solimena et al., 1996, "From Th1 to Th2: Diabetes immunotherapy shifts gears" *Nature Medicine* 2–12:1311–1312.

Srivastava et al., 1986, "Tumor rejection antigens of chemically induced sarcomas of inbred mice", *Proc. Natl. Acad. Sci.* 83:3407–3411.

Sztankay et al., 1994, "Interferon Gamma and Iodide Increase the inducibility of the 72 kD Heat Shock Protein in the Cultured Human Thyroid Epithelial Cells" *J. of Autoimmunity* 7:219–230.

Tan et al., 1995, "CD4$^+$β Islet Cell–reactive T Cell Clones that Suppress Autoimmune Diabetes in Nonobese Diabetic Mice" *J. Exp. Med.* 182:87–97.

Tisch et al., 1993, "Immune response to glutamic acid decarboxylase correlates with insulitis in non–obese diabetic mice", *Nature* 366:72–75.

J.A. Todd, 1990, "Genetic control of autoimmunity in type 1 diabetes",*Immunology Today* 11:122–129.

Tyden et al., 1996, "Recurrence of autoimmune diabetes mellitus in recipients of cadaveric pancreatic grafts",*The New England Journal of Medicine* 335:860–863.

Udono and Srivastava, 1993, "Heat shock protein 70–associated peptides elicit specific cancer immunity", *J. Exp. Med.* 178:1391–1396.

Utsugi et al., 1994, "Prevention of recurrent diabetes in syngenic islet–transplanted NOD mice by transfusion of autoreactive T lymphocytes", *Transplantation* 57:1799–1804.

Van Bleek and Nathenson, 1990, "Isolation of an endogenously processed immunodominant viral peptide from the class I H–2K$^b$ molecule", *Nature* 348:213–216.

VanBogelen et al., 1987, "Induction of the heat shock regulon does not produce thermotolerance in *Escherichia coli*", *Genes & Development* 1:525–531.

van Eden et al., 1988, "Cloning of the mycobacterial epitope recognized by T lymphocytes in adjuvant arthritis", *Nature* 331:171–173.

Verge et al., 1996, "Prediction of type I diabetes in first–degree relatives using a combination of insulin, GAD, and ICA512bdc/IA–2 autoantibodies", *Diabetes* 45:926–933.

von Herrath et al., 1995, "Coexpression of B7–1 and viral ("self") transgenes in pancreatic β cells can break peripheral ignorance and lead to spontaneous autoimmune diabetes", *Immunity* 3:727–738.

Welch and Suhan, 1985, "Morphological study of the mammalian stress response: Characterization of changes in cytoplasmic organelles, cytoskeleton, and nucleoli, and appearance of intranuclear actin filaments in rat fibroblasts after heat–shock treatment", *The Journal of Cell Biology* 101:1198–1211.

W. J. Welch, 1993, "How cells respond to stress", *Scientific American* pp. 56–64.

Yamazaki et al., 1989, "Nucleotide sequence of a full–length cDNA for 90 kDa heat–shock protein from human peripheral blood lymphocytes", *Nucleic Acids Research* 17:7108.

R.A. Young, 1990, "Stress proteins and immunology", *Annu. Rev. Immunol.* 8:401–420.

Zipris et al., 1991, "Defective thymic T cell activation by concanavalin A and anti–CD3 in autoimmune nonobese diabetic mice", *The Journal of Immunology* 146:3763–3771.

International Search Report dated Jan. 20, 1999 of corresponding PCT Application No. PCT/US98/21706 (citing references AR and DR).

METHOD AND COMPOSITIONS FOR THE TREATMENT OF AUTOIMMUNE DISEASE USING HEAT SHOCK PROTEINS

This invention was made with government support under grant numbers CA44786 and CA64394 awarded by the National Institutes of Health. The government has certain rights in the invention.

1. INTRODUCTION

The present invention relates to methods for treatment of autoimmune disease, including, but not limited to, autoimmune diabetes (i.e., juvenile diabetes or type I diabetes). In the practice of the treatment of autoimmune disease, compositions of complexes of heat shock/stress protein (hsps) including, but not limited to, gp96, hsp90, and hsp70, either alone or in combination with each other, noncovalently bound to antigenic molecules, are used to suppress the autoimmune response. Alternatively, compositions containing un-complexed stress proteins (i.e., free of antigenic molecules) are also used to suppress the immune response.

2. BACKGROUND OF THE INVENTION

Autoimmune diseases result from an abnormal immune response to self antigens. In autoimmune diseases in which the destruction of self tissue results in a metabolic deficiency, some treatment approaches are directed at replacing the deficient element. For example, patients suffering from insulin dependent diabetes mellitus (IDDM) are treated by administering insulin, and pernicious anemia patients are treated with vitamin $B_{12}$. Even under the best of circumstances, such treatments do not even address, much less reverse, the underlying immunological cause of the deficiency.

Immunological control strategies primarily have been directed either at specific, individual antigens, or at general regulatory processes. As discussed in more detail below, approaches directed at specific antigens first require accurate identification of the offending antigen. Furthermore, many pathological autoimmune responses target more than one single antigen, complicating both the process of antigen identification and the treatment strategy. Also discussed below, immunoregulatory approaches such as treatment with immunosuppressive or anti-inflammatory drugs invariably lead to detrimental effects owing to the systemic influence of the agents on the immune system.

2.1. Immunoregulation in Autoimmune Disease

Insulin is produced in the islets of Langerhans in the pancreas. Human autoimmune type I insulin-dependent diabetes mellitus (IDDM) is characterized by progressive autoimmune destruction of the pancreatic beta-cells in the islets of Langerhans by autoreactive T cells and antibodies. This destructive course is thought to be generated through a break in the peripheral tolerance or a defective clonal deletory mechanism. Non-obese diabetic (NOD) mice are classical murine models which spontaneously develop autoimmune type I IDDM with a similar immunopathological profile to human IDDM (Makino, S., et al., 1985, Current Topics In Clinical And Experimental Aspects of Diabetes (Elsevier: Amsterdam). Development of IDDM in both mice and humans is under polygenic control. IDDM results from CD4, CD8, and macrophage-mediated destruction of pancreatic islet cells (beta cells) (Castano & Eisenbarth, 1990, Ann Rev Immunol 8: 647–79; Haskins et al., 1990, Science 249: 1433–36; Nakano et al., 1991, J. Exp. Med. 173: 1091–7). Destruction of beta cells is mediated by MHC-dependent cytotoxicity. Beta cell auto-antigen specific T cells have been implicated in the pathogenesis of IDDM (Reich et al., 1993, Nature 341: 326–9; Tisch et al., 1993, Nature 366: 72–5; Kaufmen et al., 1993, Nature 366: 69–72). T cell autoreactivity is currently assumed to be due to thymic defect and/or peripheral activation of regulatory T cells secondary to altered production of cytokines (Serreze and Leiter, et al., 1988, J. Immunol. 140: 3801; Serreze et al., 1993, J. Immunol. 150: 2534; Serreze, et al., 1993, Proc. Natl. Acad. Sci. USA 90: 9625; Zipris, et al., 1991, J. Immunol. 146: 3763; Rapoport, et al., 1993, J. Exp. Med. 178: 87).

Susceptibility to IDDM in humans and NOD mice, is strongly linked to the expression of an MHC class II beta chain that lacks the usual aspartic acid residue at position 57 (Asp-57) (Todd, J. A., 1990, Immunol. Today 11: 122–9). In fact, expression of the transgenic class II beta chain containing the Asp-57 protects the NOD mice from spontaneous development of IDDM (Nishimoto et al., 1987, Nature 328:432–4; Bohme, et al., 1990, Science 249:293–5; Miyazaki et al., 1990, Nature 345:722–4; Slattery et al., 1990, Nature 345: 724–6; Singer, et al., 1993, Proc. Natl. Acad. Sci. USA 90:9566–70).

Regulatory T cell-induction has been implicated in resistance to experimentally induced autoimmune encephalitis (EAE) that develops following recovery from an acute episode (Hamaguchi and Leiter, 1990, Diabetes 39: 415; Lider, et al., 1988, Science 239: 181). Tan et al. suggest that the suppressor population is of the Th1 type (Tan et al., 1995, J. Exp. Med. 182: 87–97). However, controversy surrounds the exact type and nature of these cells. Some reports (Boitard, et al., 1989, J. Exp. Med. 169: 1669–1680; Akhtar, et al., 1995, J. Exp. Med. 182: 87–97) assert they are CD4+, whereas others attribute the effect to a wide variety of cloned T cells (Reich, et al., 1989, Diabetes 38: 1647–1651; Pankewycz, et al., 1993, Eur. J. Immunol. 22: 2017–2023; Chosich and Harrison, 1993, Diabetologica 36: 716–721; and Utsugi, et al., 1994, Transplantation (Balt) 57: 1799–1804), underscoring the diversity of regulatory T cells in general, and the uncertainty of their potential roles in suppression of autoimmune disease.

Attempts have been made to effect such induction of regulatory T cells through systemic administration of cytokines that mediate a broad-based suppression. Such therapies, however, are too nonspecific and are frequently associated with adverse side-effects.

2.2. Mycobacterial Hsp65 in Autoimmune Arthritis

Adjuvant arthritis in rats is induced by inoculation with various mycobacteria. Such induced arthritis can be suppressed by administration of hsp65 (also referred to as the 64 kD Antigen A) of *Mycobacterium bovis*, i.e. BCG (U.S. Pat. No. 5,354,691; U.S. Pat. No. 5,268,170). BCG is a commonly used adjuvant. BCG hsp65 is identical in amino acid sequence to hsp65 of *Mycobacterium tuberculosis* (Shinnick et al., 1987, Infect. Immun. 55: 1932–1935). U.S. Pat. No. 5,268,170 discloses methods of treatment or prophylaxis of "arthritis-type autoimmune diseases" using this protein.

The human homolog of mycobacterial hsp65 does not appear to be an autoantigen involved in the corresponding human disease, rheumatoid arthritis (in contrast to the role of hsp60 in IDDM discussed in Section 2.3, below). A T-cell epitope in adjuvant arthritis has been identified as the fragment of *Mycobacterium tuberculosis* (or BCG) hsp65 from amino acid 180–188 (see Elias et al., 1991, Proc. Natl.

Acad. Sci. USA 88: 3088–3091, at page 3091, citing van Eden et al., 1988, Nature 331: 171–173). Cross-reactivity between this mycobacterial hsp65 and any self protein apparently results from chance homology between this peptide and some unrelated self protein—since human hsp65 lacks this peptide (see Elias et al., 1991, supra, at page 3091, citing Jindal, et al., 1989, Mol. Cell. Biol. 9: 2279–2283). Accordingly, Elias et al., 1991, supra, reports at page 3091 that rat arthritogenic clone A2b does not respond to human hsp65.

2.3. Heat Shock Proteins As Autoantigens

Self heat shock proteins (hsps) were briefly suggested as possible immunotherapeutic agents against autoimmune disease (International Publication No. WO 89/12455, dated Dec. 28, 1989). This suggestion was based on the precondition that the self stress proteins were the targets of the autoimmune disease in question (International Publication No. WO 89/12455, at page 12, line 7 to page 14, line 23, see especially page 13, lines 11–18). The speculative suggestions contained in International Publication No. WO 89/12455, in view of the lack of practical guidance provided therein, are not instructive for the treatment of autoimmune diseases, either within the context of autoantigen targeted therapy, or as a more general approach.

One particular hsp has been identified as containing a specific autoantigen which is a target of autoimmune IDDM response. The use of *Mycobacterium tuberculosis* hsp65 (also referred to as hsp60) in treating IDDM in NOD mice was reported (Elias et al., 1990, Proc. Natl. Acad. Sci. USA 87: 1576–1580). This report, however, was limited to studying hsp65 as corresponding to a single, unique autoantigen, and not in any way as an immunomodulator. The method was determined not to be applicable to other stress proteins (Elias, et al., 1990, supra, at page 1579).

Further studies were reported using peptide p277, which is a fragment of human hsp60 and has been proposed to contain an epitope corresponding to the key epitope of *M. tuberculosis* hsp65 (U.S. Pat. No. 5,578,303; Elias and Cohen, 1995, Diabetes 44: 1132–1138). U.S. Pat. No. 5,578,303 proposes that the human hsp60 protein "can be used therapeutically" in the treatment of IDDM; no data in which the human hsp60 protein is used is presented (see Example 11, at column 12).

A general problem with attempting to induce tolerance to an autoantigen of a particular disease is that either prior to, or instead of, achieving such tolerance, the adiministration of the autoantigen may induce the disease by enhancing the destructive immune response against the target tissue. For example, administration of either *M. tuberculosis* hsp65 or p277 can lead to a transient, monophasic hyperglycemia prior to protection (Elias et al., 1990, supra; Elias, et al., 1995, Eur. J. Immunol. 25: 28512857; U.S. Pat. No. 5,578, 303). There is a risk, therefore, of at least a short term exacerbation of disease from such autoantigen administration, making its applicability problematic.

Furthermore, there are at least 12 specific autoantigens and peptides thereof that are targets of IDDM autoimmune response (Solimena and De Camilli, 1996, Nature Medicine 2: 1311). Treatment with p277 alone would not address disorders involving other autoantigens. An effective therapy using peptide autoantigens as immunogens would entail identifying the particular antigen or set of antigens that is the target for a particular IDDM patient.

Thus, the approaches discussed in these studies at best are either too general (e.g., systemic cytokine administration) or too specific (e.g., based on a single autoantigen) to provide practical, effective treatment of autoimmune disease.

Citation or identification of any reference herein shall not be construed as an admission that such reference is available as prior art to the present invention.

3. SUMMARY OF THE INVENTION

The present invention relates to compositions and methods for the treatment of autoimmune disease. Treatment regimens include the administration of heat shock proteins (hsps), including but not limited to gp96, hsp90, and hsp70. Because the protection is based on the hsp, the effectiveness of the treatment is general—unlike previous approaches, it is not limited to a specific autoantigen or a specific autoimmune disease. The effectiveness of the hsp administration is not dependent on the organ from which the hsp was obtained. Accordingly, the treatment regimens disclosed are useful for the treatment of a variety of autoimmune diseases.

In a preferred embodiment, the treatment regimens provided herein comprise administration of the hsps after the onset of the autoimmune response; i.e., after the specific immune response has already developed. Hsp administration results in regulation of the activity of the relevant, pathologically active effector cells. Thus, the treatment methods of the present invention exploit not only the general properties of hsps but also the specificity of the naturally arisen pathological immune response. Therefore, the treatment methods of the invention are more specific than common cytokine approaches to induction of suppression which are excessively systemic. The hsps used in accordance with the invention exert a more local and targeted transforming effect at the site of autoimmune cellular activity.

In a preferred embodiment, the methods for treatment of autoimmune disease provided herein are directed at reversing the autoimmune response after its onset. Thus, the treatment regimens disclosed herein have the additional advantage over prophylactic methods of being therapeutic. In a preferred embodiment wherein autoimmune diabetes is treated, the hsp is preferably administered no earlier than the period just prior to the onset of glycosuria.

Particular compositions of the invention and their properties are described in the sections and subsections which follow. Optimal doses of hsp administered for treatment of autoimmune disease are provided. In general, the dosages for use in suppressing the immune response are higher than those typically used for generating an immune response. In addition, the invention provides pharmaceutical formulations for administration of the compositions in appropriate dosages. The invention also provides routes of administration of the compositions used for treatment of autoimmune disease.

The example presented in Section 6, below, demonstrates the use of compositions comprising gp96 in the immunotherapeutic treatment of IDDM in a mouse model.

4. BRIEF DESCRIPTION OF THE FIGS.

Figure 1B:
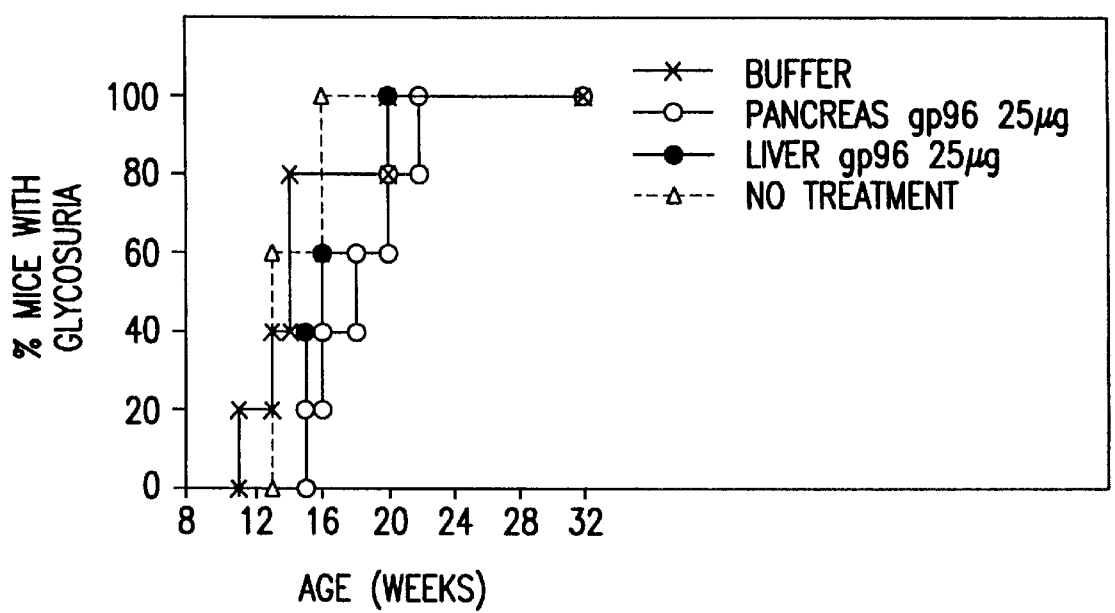
Figure 1C:
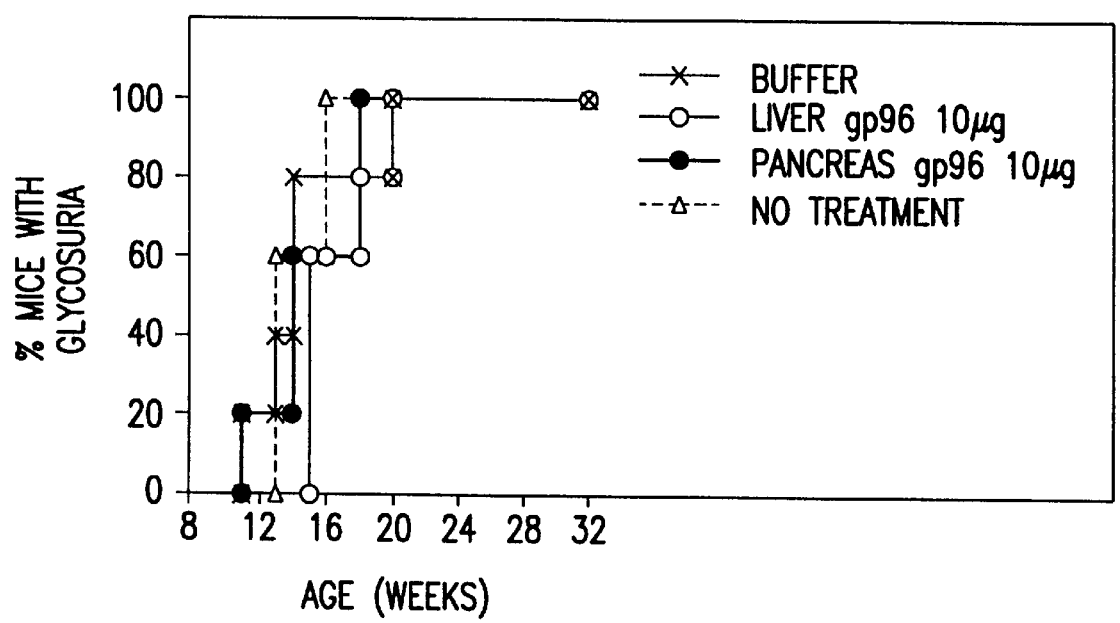

FIGS. 1A–C. Effect of dosage and tissue origin of gp96 used in immunization on the development of diabetes in non-obese diabetic (NOD) mice. Age of mice in weeks is plotted on the X-axis. Percent of mice with glycosuria is plotted on Y-axis. For each experiment, mice receiving no treatment and treatment with phosphate buffered saline (PBS) alone served as controls. Key: x=PBS alone; ○=Pancreas derived gp96; ●=Liver derived gp96; ◇=No Treatment (FIG. A only); ∆=No treatment (FIGS. 1B and 1C). FIG. 1A: pancreas and liver derived gp96 were each administered in a dose of 100 μg subcutaneously. FIG. 1B: pancreas and liver derived gp96 were each administered in a dose of 25 μg subcutaneously. FIG. 1C: pancreas and liver derived gp96 were each administered in a dose of 10 μg subcutaneously.

Figure 2A:
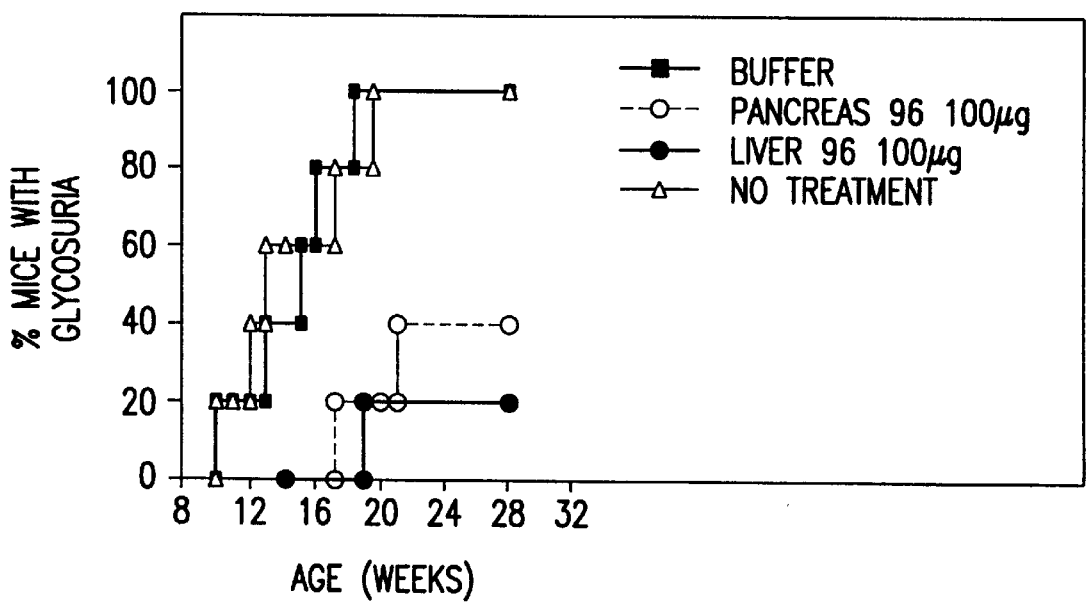
Figure 2B:
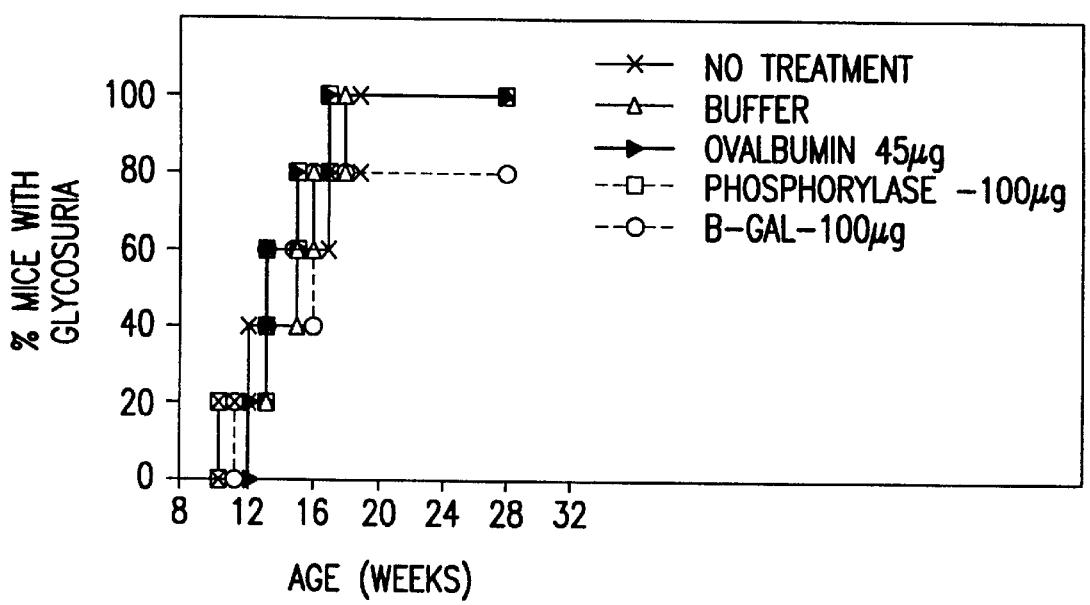

FIGS. 2A–B. Specific effectiveness of gp96 immunization as compared with immunization with other proteins. Age of mice in weeks is plotted on the X-axis. Percent of mice with glycosuria is plotted on Y-axis. For each experiment, mice receiving no treatment and treatment with phosphate buffered saline (PBS) alone served as controls. FIG. 2A: liver and pancreas derived gp96 were each administered in a dose of 100 μg. Key for FIG. 2A: Δ=No treatment; ■=PBS alone; ●=Liver derived gp96; ○=Pancreas derived gp96. FIG. 2B: The following non-heat shock proteins were compared to controls: ovalbumin (45 μg dose), phosphorylase-b (100 μg dose), and β-galactosidase (100 μg). Key for FIG. 2B: x=No Treatment; Δ=Buffer alone; ▶=Ovalbumin; □=Phosphorylase-b; ○=galactosidase.

Figure 3A:
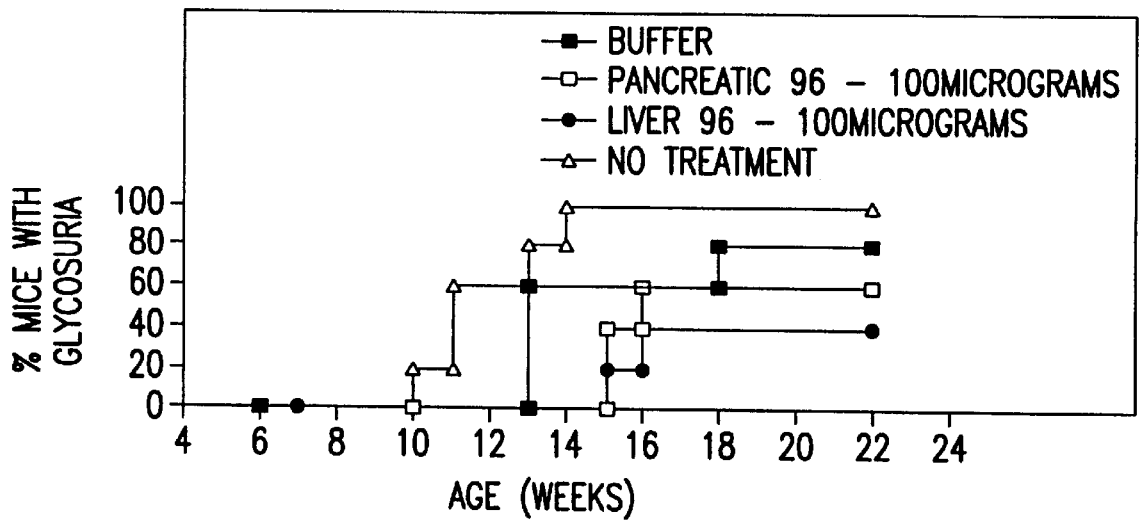
Figure 3B:
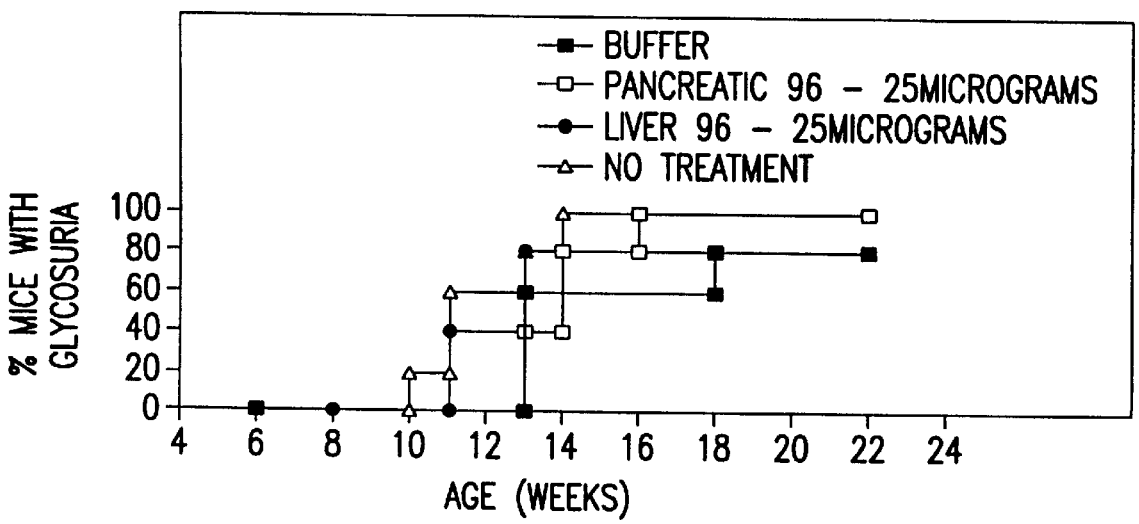
Figure 3C:
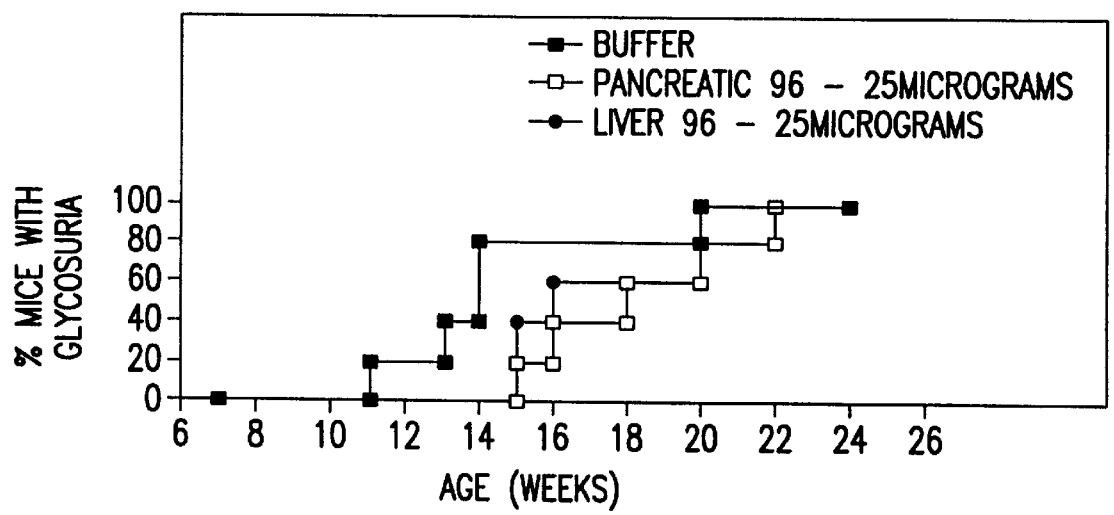
Figure 3D:
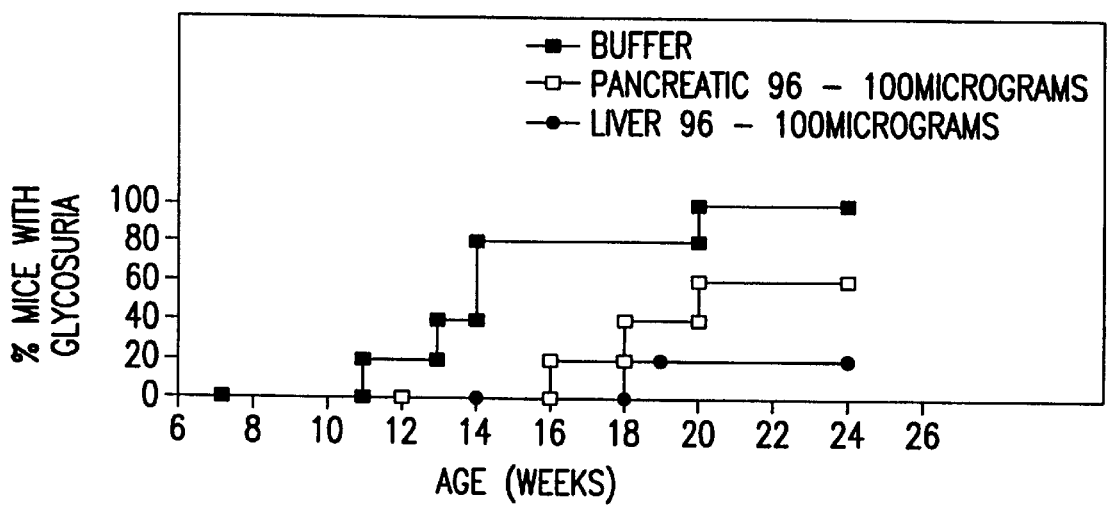

FIGS. 3A–B. Effect of age of animal at time of immunization with gp96. Age of mice in weeks is plotted on the X-axis. Percent of mice with glycosuria is plotted on Y-axis. For each experiment, mice receiving no treatment and treatment with phosphate buffered saline (PBS) alone served as controls. Key: ■=PBS alone; □=Pancreas derived gp96; ●=Liver derived gp96; Δ=No treatment. FIG. 3A: Mice received at 4 weeks of age and immunized at 5 weeks of age. Top graph: pancreas and liver derived gp96 each administered in 100 μg dose. Bottom graph: pancreas and liver derived gp96 each administered in 25 μg dose. FIG. 3B: Mice received at 8 weeks of age and immunized at 8 weeks of age. Top graph: pancreas and liver derived gp96 each administered in 25 μg dose. Bottom graph: pancreas and liver derived gp96 each administered in 100 μg dose.

Figure 4:
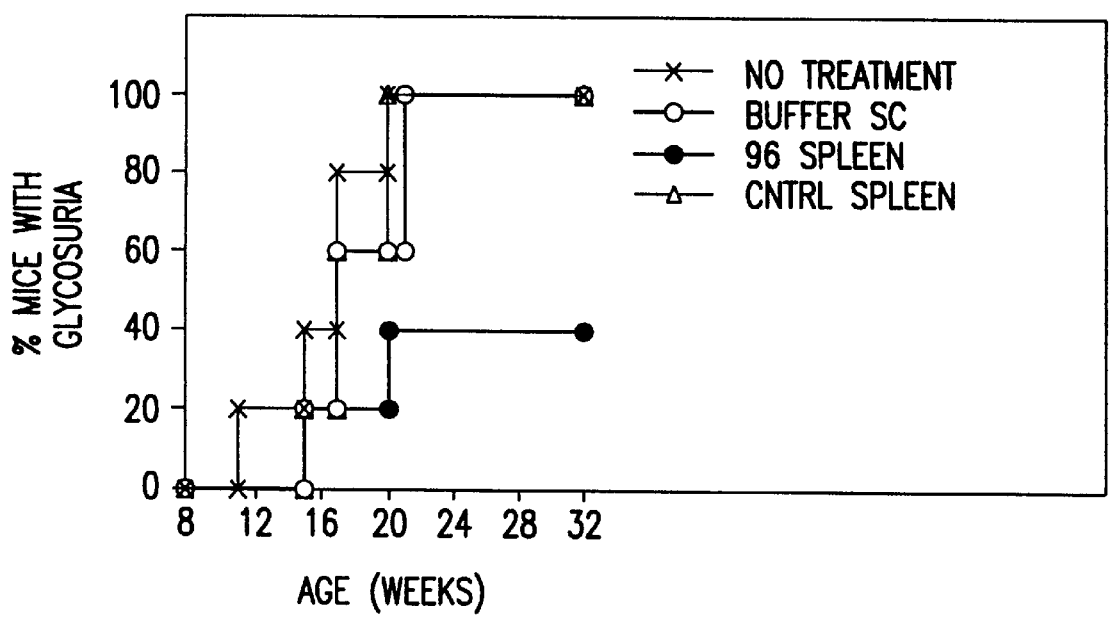

FIG. 4. Adoptive transfer of gp96-mediated protection against diabetes. Age of mice in weeks is plotted on the X-axis. Percent of mice with glycosuria is plotted on Y-axis. Key: x=No treatment; ○=Buffer SC (0.7 M phosphate buffer used for reconstitution of hsp-peptide complexes); ●=Spleen cells from gp96 treated donor; Δ=Spleen control cells (from pre-diabetic untreated NOD/LtJ mice 6–8 weeks of age).

Figure 5A:
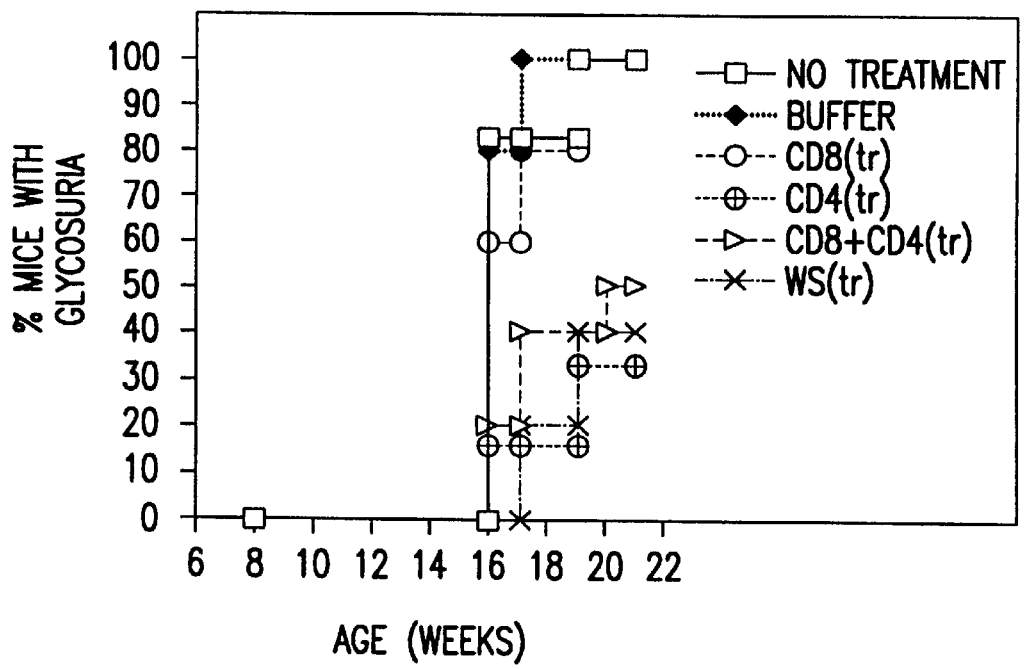
Figure 5B:
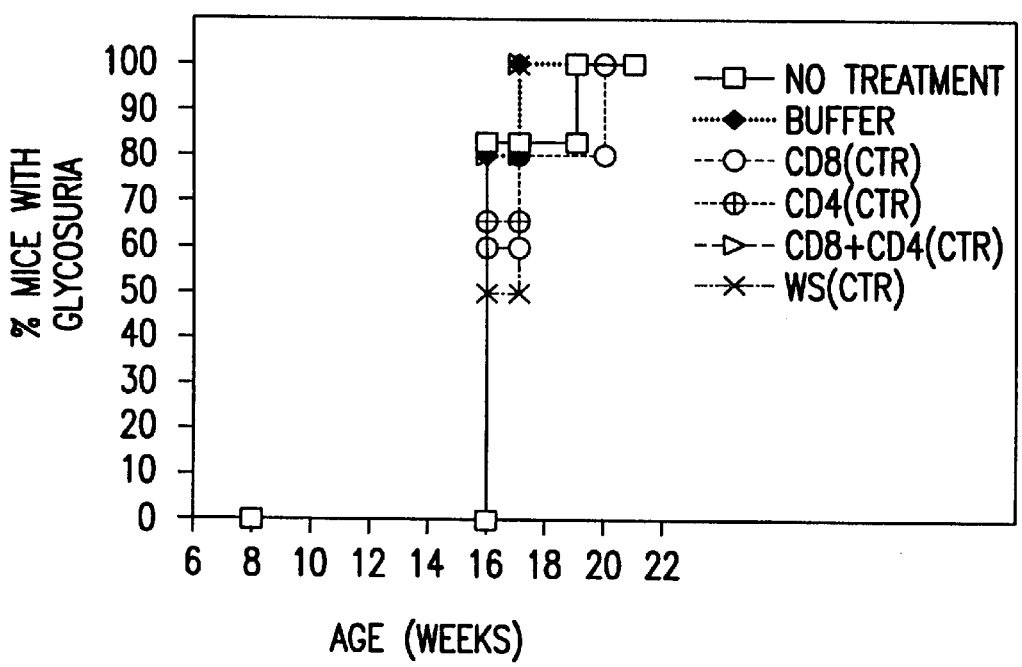

FIGS. 5A–B. Panel A—Adoptive transfer from mice treated with gp96-peptide complex. Panel B—Adoptive transfer from control mice. Key: □=No treatment; ◆=Buffer SC (0.7 M phosphate buffer used for reconstitution of hsp-peptide complexes); ○=CD8+(CTR); ⊕=CD4+ (CTR); ▷=CD8+ and CD4+ (CTR); x=Spleen control cells (from prediabetic untreated NOD/LtJ mice 6–8 weeks of age).

5. DETAILED DESCRIPTION OF THE INVENTION

Methods and compositions for the treatment of autoimmune disease are described. The invention is based, in part, on newly discovered treatment regimens which provide protection against autoimmune disease. The treatment regimens comprise the administration of hsps, optionally complexed noncovalently with antigenic molecules.

The hsps administered in accordance with the invention are ideal interventional agents against autoimmunity. In specific embodiments, such administered hsps 1) trigger protective immunoregulatory mechanisms effective when administered after the onset of autoimmune damage and, therefore, are immunotherapeutic, as opposed to prophylactic; 2) are effective for long-term protection; 3) effect antigen-specific immune suppression via antigen presenting cells (APCS) which trigger production of suppressor CD4+ C.ells that inactivate autoreactive T cells; 4) have a more general effect than individual administered autoantigens, and thus do not require identification of individual autoantigens for effectiveness; 5) nonetheless, have an effect that is specific to at least a substantial portion of the autoantigens that activate autoreactive T cells; 6) are less physiologically disruptive than such non-specific agents as cytokines, because the effect of hsps on the cytokine milieu is mediated through the endogenous, local, cellular response instead of systemically; 7) are of mammalian origin; and 8) are adjuvant free.

Administration of hsps in accordance with the methods described below are a novel immunotherapeutic modality, ideal for the treatment of autoimmune diabetes and other autoimmune diseases as well. In addition, the hsp-based immunotherapeutic methods detailed below are useful for prevention and treatment of rejection of transplanted tissues or organs, such as tissues transplanted to replace those being damaged by autoimmune disease, including but not limited to transplanted islet cells to treat IDDM.

In accordance with the invention, hsps, either uncomplexed or complexed with antigenic molecules, are administered to provide therapeutic treatment or, alternatively, prophylactic protection of autoimmune disease.

"Antigenic molecule" as used herein refers to the peptides with which the hsps are endogenously associated in vivo (e.g., in autoimmune target cells) as well as exogenous antigens/immunogens (i.e., with which the hsps are not complexed in vivo) or antigenic/immunogenic fragments and derivatives thereof.

The hsps of the present invention that can be used include but are not limited to, gp96, hsp90, and hsp70, either alone or in combination with each other. Preferably, the hsps are human hsps.

Heat shock proteins, which are also referred to interchangeably herein as stress proteins, useful in the practice of the instant invention can be selected from among any cellular protein that satisfies any one of the following criteria. A heat shock protein is characterized by having its intracellular concentration increase when a cell is exposed to a stressful stimuli, by being capable of binding other proteins or peptides, by being capable of releasing the bound proteins or peptides in the presence of adenosine triphosphate (ATP) or low pH, or by having at least 35% homology with any cellular protein having any of the above properties.

The first stress proteins to be identified were the heat shock proteins (hsps). As their name implies, hsps are synthesized by a cell in response to heat shock. To date, three major families of hsp have been identified based on molecular weight. The families have been called hsp60, hsp70 and hsp90 where the numbers reflect the approximate molecular weight of the stress proteins in kilodaltons. Mammalian hsp90 and gp96 each are members of the hsp90 family. Many members of these families were found subsequently to be induced in response to other stressful stimuli including, but not limited to, nutrient deprivation, metabolic disruption, oxygen radicals, and infection with intracellular pathogens. (See Welch, May 1993, *Scientific American* 56–64; Young, 1990, *Annu. Rev. Immunol.* 8:401–420; Craig, 1993, *Science* 260:19021903; Gething, et al., 1992, *Nature* 355:33–45; and Lindquist, et al., 1988, *Annu. Rev. Genetics* 22:631–677), the disclosures of which are incorporated herein by reference. It is contemplated that hsps/stress proteins belonging to all of these three families can be used in the practice of the instant invention.

The major hsps can accumulate to very high levels in stressed cells, but they occur at low to moderate levels in cells that have not been stressed. For example, the highly inducible mammalian hsp70 is hardly detectable at normal temperatures but becomes one of the most actively synthesized proteins in the cell upon heat shock (Welch, et al., 1985, *J. Cell. Biol.* 101:1198–1211). In contrast, hsp90 and hsp60 proteins are abundant at normal temperatures in most, but not all, mammalian cells and are further induced by heat (Lai, et al., 1984, *Mol. Cell. Biol.* 4:2802–10; van Bergen en Henegouwen, et al., 1987, *Genes Dev.* 1:525–31).

Heat shock proteins are among the most highly conserved proteins in existence. For example, DnaK, the hsp70 from *E. coli* has about 50% amino acid sequence identity with hsp70 proteins from excoriates (Bardwell, et al., 1984, *Proc. Natl. Acad. Sci.* 81:848–852). The hsp60 and hsp90 families also show similarly high levels of intra families conservation (Hickey, et al., 1989, *Mol. Cell. Biol.* 9:2615–2626; Jindal, 1989, *Mol. Cell. Biol.* 9:2279–2283). In addition, it has been discovered that the hsp60, hsp70 and hsp90 families are composed of proteins that are related to the stress proteins in sequence, for example, having greater than 35% amino acid identity, but whose expression levels are not altered by stress. Therefore it is contemplated that the definition of stress protein, as used herein, embraces other proteins, muteins, analogs, and variants thereof having at least 35% to 55%, preferably 55% to 75%, and most preferably 75% to 85% amino acid identity with members of the three families whose expression levels in a cell are enhanced in response to a stressful stimulus. The purification of stress proteins belonging to these three families is described below.

Preferably, the hsp used in accordance with the invention is not a specific autoantigen of the disease which is being treated. In a specific embodiment, the hsp used in accordance with the invention for the treatment of autoimmune disease is not a member of the hsp60 family. In a specific embodiment for the treatment of IDDM, the hsp used in accordance with the invention is not a member of the hsp60 family. In another specific embodiment, e.g. for the treatment of IDDM, the hsp used in accordance with the invention is not hsp65 of *Mycobacterium tuberculosis*, which is identical in sequence to hsp65 of *Mycobacterium bovis*, i.e. BCG (Shinnick et al., 1987, Infect. Immun. 55: 1932–1935). In a specific emobodiment, e.g. for the treatment of arthritis-type autoimmune disease, the hsp used in accordance with the invention is not a member of the hsp60 family. In another specific embodiment, e.g., for the treatment of arthritis-type autoimmune disease, the hsp used in accordance with the invention is not hsp65 of *Mycobacterium tuberculosis*, which is identical in sequence to hsp65 of *Mycobacterium bovis*, i.e. BCG (Shinnick et al., 1987, supra). In yet another specific embodiment, the hsp used in accordance with the invention for the treatment of autoimmune disease is not a mycobacterial protein. In another specific embodiment, the hsp used in accordance with the invention for the treatment of autoimmune disease is not a mycobacterial hsp60. In still another specific embodiment, the hsp used in accordance with the invention is a mammalian hsp.

The immunogenic hsp-peptide complexes of the invention include any complex containing an hsp and a peptide that is capable of inducing an immune response or immunotolerance in a mammal. The peptides are preferably noncovalently associated with the hsp. Preferred complexes include, but are not limited to, hsp90-peptide, hsp70-peptide and hsp60peptide complexes. For example, an hsp called gp96 which is present in the endoplasmic reticulum of eukaryotic cells and is related to the cytoplasmic hsp90's (i.e., is a member of the hsp90 family) can be used to generate an effective vaccine containing a gp96-peptide complex. In a specific embodiment, hsps complexed to the peptides with which they are endogenously associated are used, rather than hsps not so complexed, for purposes of convenience since the endogenous peptides copurify with the hsps.

Although the hsps can be allogeneic to the patient, in a preferred embodiment, the hsps are autologous to (derived from) the patient to whom they are administered. The hsps and/or antigenic molecules can be purified from natural sources, chemically synthesized, or recombinantly produced. The invention provides methods for determining doses for autoimmune disease immunotherapy by evaluating the optimal dose of hsp, both unbound and noncovalently bound to peptide, in experimental tumor models and extrapolating the data.

The therapeutic regimens and pharmaceutical compositions of the invention can be used with additional immune response enhancers or biological response modifiers including, but not limited to, the cytokines IFN-α, IFN-γ, IL-2, IL-4, IL-6, TNF, or other cytokine affecting immune cells. In accordance with this aspect of the invention, the hsp either uncomplexed or complexed with antigenic molecule is administered in combination therapy with one or more of these cytokines.

Accordingly, the invention provides methods of preventing and treating autoimmune disease in an individual comprising administering a composition which elicits specific immunotolerance to the target host cells or tissue.

The invention further relates to administration of compositions comprising hsps, either uncomplexed or complexed to peptides, to individuals at enhanced risk of autoimmune disease due to familial history or environmental risk factors.

5.1. Target Autoimmune Diseases

Autoimmune diseases that can be treated by the methods of the present invention include, but are not limited to, insulin dependent diabetes mellitus (i.e., IDDM, or autoimmune diabetes), multiple sclerosis, systemic lupus erythematosus, Sjogren's syndrome, scleroderma, polymyositis, chronic active hepatitis, mixed connective tissue disease, primary biliary cirrhosis, pernicious anemia, autoimmune thyroiditis, idiopathic Addison's disease, vitiligo, gluten-sensitive enteropathy, Graves' disease, myasthenia gravis, autoimmune neutropenia, idiopathic thrombocytopenia purpura, rheumatoid arthritis, cirrhosis, pemphigus vulgaris, autoimmune infertility, Goodpasture's disease, bullous pemphigoid, discoid lupus, ulcerative colitis, and dense deposit disease. The diseases set forth above, as referred to herein, include those exhibited by animal models for such diseases, such as, for example non-obese diabetic (NOD) mice for IDDM and experimental autoimmune encephalomyelitis (EAE) mice for multiple sclerosis.

The methods of the present invention can be used to treat such autoimmune diseases by reducing or eliminating the immune response to the patient's own (self) tissue, or, alternatively, by reducing or eliminating a pre-existing autoimmune response directed at tissues or organs transplanted to replace self tissues or organs damaged by the autoimmune response.

5.2. Obtaining Therapeutic Compositions for Suppression of Autoimmune Response The hsps used in accordance with the invention can be complexed with antigenic molecules (e.g., peptides), or uncomplexed. Whether complexed or not, the hsps can be native (non-recombinant) or recombinant. The antigenic molecules can be endogenous, i.e., naturally associated with hsp intracellularly. Alternatively, the antigenic molecules can be exogenous, i.e., not naturally occurring in a noncovalent complex with hsps, or eluted from a cellularly derived noncovalent complex with hsps and reconstituted with other hsps in vitro. Preferably, the hsp, or complex, as the case may be, is used in purified form, preferably to homogeneity as viewed on a polyacrylamide gel, or to at least 60%, 70%, 80%, or 90% of total protein.

The hsp-peptide complexes can be isolated as such from cells wherein the hsp and antigenic molecule are produced. Hsps or exogenous antigenic molecules can be produced in the cell by recombinant expression of a gene encoding that component (either hsp or antigenic molecule), or can be isolated from native sources. The hsps and exogenous antigenic molecule components can be produced and isolated independently and complexed in vitro. Alternatively, complexes of hsps and endogenous peptides can be isolated from cells. In a preferred embodiment for in vitro complexing of hsps and exogenous antigenic molecules, the hsp component is first isolated from cells as a complex, and then purified away from the noncovalently bound endogenous peptide with which it is complexed, prior to complexing in vitro with the exogenous antigenic molecule of interest. Alternatively, the hsp component is first isolated from cells as a complex, and then the noncovalently bound endogenous peptide with which it is complexed is exchanged in vitro with the exogenous antigenic molecule of interest.

Accordingly, the protocols described herein can be used to isolate and produce purified hsps or purified complexes of hsps and antigenic molecules.

Uncomplexed endogenous hsps and endogenous hsps complexed with antigenic molecules can be isolated from any eukaryotic cells, including but not limited to, tissues, isolated cells, and immortalized eukaryotic cell lines. The tissue source need not be the same as the tissue which is targeted by the subject autoimmune response. Suitable source tissues include, but are not limited to liver, or pancreas, or any other organ of mammalian or non-mammalian origin.

Alternatively, the hsps can be produced by recombinant DNA technology using techniques well known in the art. These methods are described in detail in Section 5.2.2, below.

Peptides derived from either a naturally expressed protein (i.e., native peptide) or from a recombinantly expressed protein can be isolated by first isolating the corresponding hsp-peptide complex and then eluting the peptide. Methods for eluting noncovalently bound peptide from the hsp-peptide complex are described in Section 5.2.4, below. Peptides can also be produced synthetically and subsequently complexed with hsps in vitro.

Methods for complexing hsps with antigenic molecules in vitro are described in Section 5.2.5, below.

The hsps to be used therapeutically, alone or complexed, can but need not be isolated from a sample from the patient to which they are then to be administered to treat or prevent autoimmune disorder, i.e., the hsps (and antigenic molecules) can be autologous or non-autologous.

5.2.1. Preparation of Hsp-Peptide Complexes

The methods described in Sections 5.2.1.1–5.2.1.3, below, can be used to isolate hsps complexed with antigenic molecules from cells, preferably from cells expressing non-recombinant hsps, although cells expressing recombinant hsps may also be used. These same methods may also be used to prepare purified hsp, by removing the endogenous antigenic molecules from the isolated complexes by methods described in Section 5.2.3, below.

5.2.1.1. Preparation and Purification of gp96-peptide Complexes

A procedure that can be used, presented by way of example and not limitation, is as follows:

A pellet of eukaryotic cells (e.g., from liver, pancreas, or any other convenient organ) is resuspended in 3 volumes of buffer consisting of 30 mM sodium bicarbonate buffer (pH 7.5) and 1 mM PMSF and the cells allowed to swell on ice 20 minutes. The cell pellet then is homogenized in a Dounce homogenizer (the appropriate clearance of the homogenizer will vary according to each cells type) on ice until >95% cells are lysed.

The lysate is centrifuged at 1,000×g for 10 minutes to remove unbroken cells, nuclei and other debris. The supernatant from this centrifugation step then is recentrifuged at 100,000×g for 90 minutes. The gp96-peptide complex can be purified either from the 100,000×g pellet or from the supernatant.

When purified from the supernatant, the supernatant is diluted with equal volume of 2× lysis buffer and the supernatant mixed for 2–3 hours at 4° C. with Con A-Sepharose® (Pharmacia, Inc., Sweden) equilibrated with PBS containing 2 mM $Ca^{2+}$ and 2 mM $Mg^{2+}$. Then, the slurry is packed into a column and washed with 1× lysis buffer until the $OD_{280}$ drops to baseline. Then, the column is washed with ⅓ C.olumn bed volume of 10% α-methyl mannoside (α-MM) dissolved in PBS containing 2 mM $Ca^{2+}$ and 2 mM $Mg^{2+}$, the column sealed with a piece of parafilm, and incubated at 37° C. for 15 minutes. Then the column is cooled to room temperature and the parafilm removed from the bottom of the column. Five column volumes of the α-MM buffer are applied to the column and the eluate analyzed by SDS-PAGE. Typically the resulting material is about 60–95% pure, however this depends upon the cell type and the tissue-to-lysis buffer ratio used. Then the sample is applied to a Mono Q® FPLC ion-exchange chromatographic column (Pharmacia, Inc., Piscataway, N.J.) equilibrated with a buffer containing 5 mM sodium phosphate, pH 7. The proteins then are eluted from the column with a 0–1 M NaCl gradient and the gp96 fraction elutes between 400 mM and 550 mM NaCl.

The procedure, however, can be modified by two additional steps, used either alone or in combination, to consistently produce apparently homogeneous gp96-peptide complexes. One optional step involves an ammonium sulfate precipitation prior to the Con A purification step and the other optional step involves DEAE-Sepharose® purification after the Con A purification step but before the Mono Q® FPLC step.

In the first optional step, the supernatant resulting from the 100,000×g centrifugation step is brought to a final concentration of 50% ammonium sulfate by the addition of ammonium sulfate. The ammonium sulfate is added slowly while gently stirring the solution in a beaker placed in a tray of ice water. The solution is stirred from about ½ to 12 hours at 4° C. and the resulting solution centrifuged at 6,000 rpm (Sorvall SS34 rotor). The supernatant resulting from this step is removed, brought to 70% ammonium sulfate saturation by the addition of ammonium sulfate solution, and centrifuged at 6,000 rpm (Sorvall SS34 rotor). The resulting pellet from this step is harvested and suspended in PBS containing 70% ammonium sulfate in order to rinse the pellet. This mixture is centrifuged at 6,000 rpm (Sorvall SS34 rotor) and the pellet dissolved in PBS containing 2 mM $Ca^{2+}$ and $Mg^{2+}$. Undissolved material is removed by a brief centrifugation at 15,000 rpm (Sorvall SS34 rotor). Then, the solution is mixed with Con A Sepharose® and the procedure followed as before.

In the second optional step, the gp96 containing fractions eluted from the Con A column are pooled and the buffer exchanged for 5 mM sodium phosphate buffer, pH 7, 300 mM NaCl by dialysis, or preferably by buffer exchange on a Sephadex® G25 column (Pharmacia, Inc., Sweden). After buffer exchange, the solution is mixed with DEAE-Sepharose® previously equilibrated with 5 mM sodium phosphate buffer, pH 10 7, 300 mM NaCl. The protein solution and the beads are mixed gently for 1 hour and poured into a column. Then, the column is washed with 5 mM sodium phosphate buffer, pH 7, 300 mM NaCl, until the absorbance at 280 nM drops to baseline. Then, the bound protein is eluted from the column with five volumes of 5 mM sodium phosphate buffer, pH 7, 700 mM NaCl. Protein containing fractions are pooled and diluted with 5 mM sodium phosphate buffer, pH 7 in order to lower the salt concentration to 175 mM. The resulting material then is applied to the Mono Q® FPLC column (Pharmacia) equilibrated with 5 mM sodium phosphate buffer, pH 7 and the protein that binds to the Mono Q® FPLC column (Pharmacia) is eluted as described before.

It is appreciated, however, that one skilled in the art can assess, by routine experimentation, the benefit of incorporating the second optional step into the purification protocol. In addition, it is appreciated also that the benefit of adding each of the optional steps will depend upon the source of the starting material.

When the gp96 fraction is isolated from the 100,000×g pellet, the pellet is suspended in 5 volumes of PBS containing either 1% sodium deoxycholate or 1% octyl glucopyranoside (but without the $Mg^{2+}$ and $Ca^{2+}$) and incubated on ice for 1 hour. The suspension is centrifuged at 20,000×g for 30 minutes and the resulting supernatant dialyzed against several changes of PBS (also without the $Mg^{2+}$ and $Ca^{2+}$) to remove the detergent. The dialysate is centrifuged at 100,000×g for 90 minutes, the supernatant harvested, and calcium and magnesium are added to the supernatant to give final concentrations of 2 mM, respectively. Then the sample is purified by either the unmodified or the modified method for isolating gp96-peptide complex from the 100,000×g supernatant, see above.

The gp96-peptide complexes can be purified to apparent homogeneity using this procedure. About 10–20 μg of gp96peptide complex can be isolated from ig cells/tissue.

5.2.1.2. Preparation and Purification of Hsp 70-peptide Complexes

The purification of hsp70-peptide complexes has been described previously, see, for example, Udono et al., 1993, *J. Exp. Med.* 178:1391–1396. A procedure that can be used, presented by way of example but not limitation, is as follows:

Initially, cells (e.g., from liver, pancreas, or any other convenient organ) are suspended in 3 volumes of 1× lysis buffer consisting of 5 mM sodium phosphate buffer, pH 7, 150 mM NaCl, 2 mM $CaCl_2$, 2 mM $MgCl_2$ and 1 mM phenyl methyl sulfonyl fluoride (PMSF). Then, the pellet is sonicated, on ice, until >99% cells are lysed as determined by microscopic examination. As an alternative to sonication, the cells can be lysed by mechanical shearing and in this approach the cells typically are resuspended in 30 mM sodium bicarbonate pH 7.5, 1 mM PMSF, incubated on ice for 20 minutes and then homogenized in a dounce homogenizer until >95% cells are lysed.

Then the lysate is centrifuged at 1,000×g for 10 minutes to remove unbroken cells, nuclei and other cellular debris. The resulting supernatant is recentrifuged at 100,000×g for 90 minutes, the supernatant harvested and then mixed with Con A Sepharose® equilibrated with phosphate buffered saline (PBS) containing 2 mM $Ca^{2+}$ and 2 mM $Mg^{2+}$. When the cells are lysed by mechanical shearing the supernatant is diluted with an equal volume of 2× lysis buffer prior to mixing with Con A Sepharose®. The supernatant is then allowed to bind to the Con A Sepharose® for 2–3 hours at 4° C. The material that fails to bind is harvested and dialyzed for 36 hours (three times, 100 volumes each time) against 10 mM Tris-Acetate pH 7.5, 0.1 mM EDTA, 10 mM NaCl, 1 mM PMSF. Then the dialyzate is centrifuged at 17,000 rpm (Sorvall SS34 rotor) for 20 minutes. Then the resulting supernatant is harvested and applied to a Mono Q® FPLC column equilibrated in 20 mM Tris-Acetate pH 7.5, 20 mM NaCl, 0.1 mM EDTA and 15 mM 2-mercaptoethanol. The column is then developed with a 20 mM to 500 mM NaCl gradient and then eluted fractions fractionated by sodium dodecyl sulfate-polyacrylamide gel electrophoresis (SDS-PAGE) and characterized by immunoblotting using an appropriate anti-hsp70 antibody (such as from clone N27F3–4, from StressGen, Victoria, British Columbia, Canada).

Fractions strongly immunoreactive with the anti-hsp70 antibody are pooled and the hsp70-peptide complexes precipitated with ammonium sulfate; specifically with a 50%–70% ammonium sulfate cut. The resulting precipitate is then harvested by centrifugation at 17,000 rpm (SS34 Sorvall rotor) and washed with 70% ammonium sulfate. The washed precipitate is then solubilized and any residual ammonium sulfate removed by gel filtration on a Sephadex® G25 column (Pharmacia). If necessary the hsp70 preparation thus obtained can be repurified through the Mono Q® FPLC column as described above.

The hsp70-peptide complex can be purified to apparent homogeneity using this method. Typically 1mg of hsp70peptide complex can be purified from 1g of cells/tissue.

The present invention further describes a rapid method for purification of hsp70-peptide complexes. This improved method comprises contacting cellular proteins with ADP or a nonhydrolyzable analog of ATP affixed to a solid substrate, such that hsp70 in the lysate can bind to the ADP or nonhydrolyzable ATP analog, and eluting the bound hsp70. A preferred method uses column chromatography with ADP affixed to a solid substratum (e.g., ADP-agarose). The resulting hsp70 preparations are higher in purity and devoid of contaminating peptides. The hsp70 yields are also increased significantly by about more than 10 fold. Alternatively, chromatography with nonhydrolyzable analogs of ATP, instead of ADP, can be used for purification of hsp70-peptide complexes.

By way of example but not limitation, purification of hsp70-peptide complexes by ADP-agarose chromatography is carried out as follows:

500 million cells (e.g., from liver, pancreas, or any other convenient organ) are homogenized in hypotonic buffer and the lysate is centrifuged at 100,000×g for 90 minutes at 4° C. The supernatant is applied to an ADP-agarose column.

The column is washed in buffer and is eluted with 5 column volumes of 3 mM ADP. The hsp70-peptide complexes elute in fractions 2 through 10 of the total 15 fractions which elute. The eluted fractions are analyzed by SDS-PAGE. The hsp70-peptide complexes can be purified to apparent homogeneity using this procedure.

5.2.1.3. Preparation and Purification of Hsp 90-peptide Complexes

A procedure that can be used to prepare hsp90-peptide complexes, presented by way of example and not limitation, is as follows:

Initially, cells (e.g., from liver, pancreas, or any other convenient organ) are suspended in 3 volumes of 1× Lysis buffer consisting of 5 mM sodium phosphate buffer (pH7), 150 mM NaCl, 2 mM $CaCl_2$, 2 mM $MgCl_2$ and 1 mM phenyl methyl sulfonyl fluoride (PMSF). Then, the pellet is sonicated, on ice, until >99% cells are lysed as determined by microscopic examination. As an alternative to sonication, the cells can be lysed by mechanical shearing and in this approach the cells typically are resuspended in 30 mM sodium bicarbonate pH 7.5, 1 mM PMSF, incubated on ice for 20 minutes and then homogenized in a dounce homogenizer until >95% cells are lysed.

Then the lysate is centrifuged at 1,000×g for 10 minutes to remove unbroken cells, nuclei and other cellular debris. The resulting supernatant is recentrifuged at 1000,000×g for 90 minutes, the supernatant harvested and then mixed with Con A Sepharose® equilibrated with PBS containing 2 mM $Ca^{2+}$ and 2 mM $Mg^{2+}$. When the cells are lysed by mechanical shearing the supernatant is diluted with an equal volume of 2× Lysis buffer prior to mixing with Con A Sepharose®. The supernatant is then allowed to bind to the Con A Sepharose® for 2–3 hours at 4° C. The material that fails to bind is harvested and dialyzed for 36 hours (three times, 100 volumes each time) against 10 mM Tris-Acetate pH 7.5, 0.1 mM EDTA, 10 mM NaCl, 1 mM PMSF. Then the dialyzate is centrifuged at 17,000 rpm (Sorvall SS34 rotor) for 20 minutes. Then the resulting supernatant is harvested and applied to a Mono Q® FPLC column equilibrated with lysis buffer. The proteins are then eluted with a salt gradient of 200 mM to 600 mM NaCl.

The eluted fractions are fractionated by SDS-PAGE and fractions containing the hsp90-peptide complexes identified by immunoblotting using an anti-hsp90 antibody such as 3G3 (Affinity Bioreagents). Hsp90-peptide complexes can be purified to apparent homogeneity using this procedure. Typically, 150–200 μg of hsp90-peptide complex can be purified from 1 g of cells/tissue.

5.2.2. Recombinant Production of Hsps

Many genes encoding hsps have been cloned and sequenced, including, for example, human hsp70 (GenBank Accession Nos. M11717 and M15432; see also Hunt and Morimoto, 1985, Proc. Natl. Acad. Sci. USA 82: 6455–6459), human hsp90 (GenBank Accession No. X15183; see also Yamazaki et al., 1989, Nucleic Acids Res. 17: 7108), and human gp96 (GenBank Accession No. M33716; see also Maki et al., 1990, Proc. Natl. Acad. Sci. USA 87: 5658–5662).

The hsps can be produced by recombinant DNA technology using techniques well known in the art. Methods which are well known to those skilled in the art can be used to construct expression vectors containing hsp coding sequences and appropriate transcriptional/translational control signals. These methods include, for example, in vitro recombinant DNA techniques, synthetic techniques and in vivo recombination/genetic recombination. See, for example, the techniques described in Sambrook et al., 1989, supra, and Ausubel et al., 1989, supra.

A variety of host-expression vector systems can be utilized to express the hsp genes. These include but are not limited to microorganisms such as bacteria (e.g., *E. coli*, B. subtilis) transformed with recombinant bacteriophage DNA, plasmid DNA or cosmid DNA expression vectors containing the hsp coding sequence; yeast (e.g. Saccharomyces, Pichia) transformed with recombinant yeast expression vectors containing the hsp coding sequence; insect cell systems infected with recombinant virus expression vectors (e.g., baculovirus) containing the hsp coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the hsp coding sequence; or mammalian cell systems (e.g. COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, for example, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the hsp coding sequence can be ligated individually into the vector in frame with the lac Z coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned hsp gene protein can be released from the GST moiety.

In an insect system, *Autographa californica* nuclear polyhedrosis virus (AcNPV) is used as a vector to express foreign genes. The virus grows in *Spodoptera frugiperda* cells. The hsp gene can be cloned individually into non-essential regions (for example the polyhedrin gene) of the virus and placed under control of an AcNPV promoter (for example the polyhedrin promoter). Successful insertion of the hsp coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (E.g., see Smith et al., 1983, J. Virol. 46: 584; Smith, U.S. Pat. No. 4,215,051).

In mammalian host cells, a number of viral-based expression systems can be utilized. In cases where an adenovirus is used as an expression vector, the hsp coding sequence can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing hsps in infected hosts. (See, e.g., Logan & Shenk, 1984, Proc. Natl. Acad. Sci. USA 81:3655–3659). Specific initiation signals may also be required for efficient translation of inserted hsp coding sequence. These signals include the ATG initiation codon and adjacent sequences. The efficiency of expression can be enhanced by the inclusion of appropriate transcription enhancer elements, transcription terminators, etc. (see Bittner et al., 1987, Methods in Enzymol. 153:516–544).

In addition, a host cell strain can be chosen which modulates the expression of the inserted sequences, or modifies and processes the hsp in the specific fashion desired. For example, choosing a system that allows for appropriate glycosylation is especially important in the case of gp96. Different host cells have characteristic and specific mechanisms for the post-translational processing and modification of proteins such as glycosylation. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, etc.

In a preferred embodiment for recombinant expression of hsps, the histidine-nickel (his-Ni) tag system is used (Janknecht, et al., 1991, Proc. Natl. Acad. Sci. USA 88: 8972–8976). In the his-Ni system, the hsp is expressed in human cell lines as a fusion protein which can be readily purified in a non-denatured form. In this system, the gene of interest (i.e., the hsp gene) is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

Kits for expressing an isolating proteins using the his-Ni system are commercially available from Invitrogen®, San Diego, Calif.

Alternatively, recombinant hsps produced in eukaryotic hosts cells as described in this section, above, can be purified according to the respective methods detailed in Section 5.2.1, above.

5.2.3. Preparation and Purification of Uncomplexed hsps

The following methods can be used to obtain uncomplexed hsps, i.e., hsps that are substantially free of noncovalently bound antigenic molecules such as peptides. The hsps can be administered in their uncomplexed form in accordance with the invention for the treatment and prevention of autoimmune disease. In addition, the uncomplexed hsps can be used to design hsp-antigenic molecule complexes by complexing them in vitro with antigenic molecules of interest, as described in Section 5.2.5, below.

5.2.3.1. General Methods

Methods which can be used to separate the hsp and antigenic molecule components of the hsp-antigenic molecule complexes from each other, include, but are not limited to, treatment of the complexes with low pH. The low pH treatment methods described in this section, below, can be used for hsp70, hsp90, or gp96. An alternative method which is preferred for isolating hsp70 from hsp-antigenic molecule complexes is provided in Section 5.2.3.2.

By way of example but not limitation, to elute the noncovalently bound antigenic molecule using low pH, acetic acid or trifluoroacetic acid is added to the purified hsp-antigenic molecule complex to give a final concentration of 10% (vol/vol) and the mixture incubated at room temperature or in a boiling water bath or any temperature in between, for minutes (See, Van Bleek, et al., 1990, *Nature* 348:213–216; and Li, et al., 1993, *EMBO Journal* 12:3143–3151). The resulting samples are centrifuged through a Centricon® 10 assembly. The high and low molecular weight fractions are recovered. The remaining large molecular weight hsp70-peptide complexes can be reincubated in low pH to remove any remaining peptides. The resulting higher molecular weight fractions containing hsp are pooled and concentrated.

5.2.3.2. Preferred Method for Preparation and Purification of Un-complexed Hsp 70

Preferably, the hsp70-peptide complex is purified as described above in Section 5.2.1.2. Once the hsp70-peptide complex is purified, the peptide is eluted from the hsp70 by either of the following two preferred methods. More preferably, the hsp70-peptide complex is incubated in the presence of ATP. Alternatively, the hsp70-peptide complex is incubated in a low pH buffer, as described in Section 5.2.2, above.

Briefly, the complex is centrifuged through a Centricon® assembly (Millipore) to remove any low molecular weight material loosely associated with the complex. The large molecular weight fraction can be removed and analyzed by SDSPAGE while the low molecular weight can be analyzed by HPLC as described below. In the ATP incubation protocol, the stress protein-peptide complex in the large molecular weight fraction is incubated with 10 mM ATP for 30 minutes at room temperature.

The resulting samples are centrifuged through a Centricon® 10 assembly as mentioned previously. The high and low molecular weight fractions are recovered. The remaining large molecular weight hsp70-peptide complexes can be reincubated with ATP to remove any remaining peptides.

The resulting higher molecular weight fractions containing hsp70 are pooled and concentrated.

5.2.4. Isolation of Antigenic Components

The methods described in Section 5.2.3, above, which can be used to isolate hsps from complexes with antigenic molecules, can similarly be used to isolate peptides and/or antigenic components from cells which may contain potentially useful antigenic determinants. Once the hsps and antigenic molecules are separated from each other into separate fractions, the fractions containing the antigenic molecules can be pooled and processed further, as described below. Once isolated, the amino acid sequence of each antigenic peptide can be determined using conventional amino acid sequencing methodologies. Such antigenic molecules can then be produced by chemical synthesis or recombinant methods, purified, and complexed to hsps in vitro.

Similarly, it has been found that potentially immunogenic peptides may be eluted from MHC-peptide complexes using techniques well known in the art (Falk, K. et al., 1990 *Nature* 348:248–251; Elliott, T., et al., 1990, *Nature* 348:195–197; Falk, K., et al., 1991, *Nature* 351:290–296).

Thus, potentially immunogenic or antigenic peptides can be isolated from either stress protein-peptide complexes or MHC-peptide complexes for use subsequently as antigenic molecules, by complexing in vitro to hsps. Exemplary protocols for isolating peptides and/or antigenic components from either of the these complexes are set forth below in Sections 5.2.4.1 and 5.2.4.2.

5.2.4.1. Peptides From Stress Protein-Peptide Complexes

The methods detailed in Section 5.2.3, above, can be used to elute the peptide from a stress protein-peptide complex. One approach involves incubating the stress protein-peptide complex in the presence of ATP. The other approach involves incubating the complexes in a low pH buffer.

Briefly the complex of interest is centrifuged through a Centricon® 10 assembly (Millipore) to remove any low molecular weight material loosely associated with the complex. The large molecular weight fraction can be removed and analyzed by SDS-PAGE while the low molecular weight can be analyzed by HPLC as described below. In the ATP incubation protocol, the stress protein-peptide complex in he large molecular weight fraction is incubated with 10 mM TP for 30 minutes at room temperature. In the low pH protocol, acetic acid or trifluoroacetic acid (TFA) is added to the stress protein-peptide complex to give a final concentration of 10% (vol/vol) and the mixture incubated at room temperature or in a boiling water bath or any temperature in between, for 10 minutes (See, Van Bleek, et al., 1990, *Nature* 348:213–216; and Li, et al., 1993, *EMBO Journal* 12:3143–3151).

The resulting samples are centrifuged through a Centricon® 10 assembly as mentioned previously. The high and low molecular weight fractions are recovered. The remaining large molecular weight stress protein-peptide complexes can be reincubated with ATP or low pH to remove any remaining peptides.

The resulting lower molecular weight fractions are pooled, concentrated by evaporation and dissolved in 0.1% TFA. The dissolved material is then fractionated by reverse phase high pressure liquid chromatography (HPLC) using for example a VYDAC® C18 reverse phase column (Separations Group, Inc., Hesperia, Calif.) equilibrated with 0.1% TFA. The bound material is then eluted at a flow rate of about 0.8 ml/min by developing the column with a linear gradient of 0 to 80% acetonitrile in 0.1% TFA. The elution of the peptides can be monitored by $OD_{210}$ and the fractions containing the peptides collected.

5.2.4.2. Peptides from MHC-peptide Complexes

The isolation of potentially immunogenic peptides from MHC molecules is well known in the art and so is not described in detail herein (See, Falk, et al., 1990, Nature 348:248–251; Rotzsche, at al., 1990, *Nature* 348:252–254; Elliott, et al., 1990, *Nature* 348:191–197; Falk, et al., 1991, *Nature* 351:290–296; Demotz, et al., 1989, *Nature* 343:682–684; Rotzsche, et al., 1990, *Science* 249:283–287, the disclosures of which are incorporated herein by reference).

Briefly, MHC-peptide complexes can be isolated by a conventional immunoaffinity procedure. The peptides then can be eluted from the MHC-peptide complex by incubating the complexes in the presence of about 0.1% TFA in acetonitrile. The eluted peptides can be fractionated and purified by reverse phase HPLC, as before.

The amino acid sequences of the eluted peptides can be determined either by manual or automated amino acid sequencing techniques well known in the art. Once the amino acid sequence of a potentially protective peptide has been determined the peptide can be synthesized in any desired amount using conventional peptide synthesis or other protocols well known in the art.

5.2.4.3. Synthetic Production of Peptides

Peptides having the same amino acid sequence as those isolated above can be synthesized by solid-phase peptide synthesis using procedures similar to those described by Merrifield, 1963, *J. Am. Chem. Soc.,* 85:2149. During synthesis, N-α-protected amino acids having protected side chains are added stepwise to a growing polypeptide chain linked by its C-terminal and to an insoluble polymeric support i.e., polystyrene beads. The peptides are synthesized by linking an amino group of an N-α-deprotected amino acid to an a-carboxy group of an N-α-protected amino acid that has been activated by reacting it with a reagent such as dicyclohexylcarbodiimide. The attachment of a free amino group to the activated carboxyl leads to peptide bond formation. The most commonly used N-a-protecting groups include Boc which is acid labile and Fmoc which is base labile.

Briefly, the C-terminal N-α-protected amino acid is first attached to the polystyrene beads. The N-α-protecting group is then removed. The deprotected α-amino group is coupled to the activated α-carboxylate group of the next N-α-protected amino acid. The process is repeated until the desired peptide is synthesized. The resulting peptides are then cleaved from the insoluble polymer support and the amino acid side chains deprotected. Longer peptides can be derived by condensation of protected peptide fragments. Details of appropriate chemistries, resins, protecting groups, protected amino acids and reagents are well known in the art and so are not discussed in detail herein (See, Atherton, et al., 1989, *Solid Phase Peptide Synthesis: A Practical Approach*, IRL Press, and Bodanszky, 1993, *Peptide Chemistry, A Practical Textbook,* 2nd Ed., Springer-Verlag).

Purification of the resulting peptides is accomplished using conventional procedures, such as preparative HPLC using gel permeation, partition and/or ion exchange chromatography. The choice of appropriate matrices and buffers are well known in the art and so are not described in detail herein.

5.2.5. In Vitro Production of Stress Protein-Antigenic Molecule Complexes

In an embodiment in which complexes of hsps and the peptides with which they are endogenously associated in vivo are not employed, and it is desired to use hsp-antigenic molecule complexes, complexes of hsps to antigenic molecules are produced in vitro. As will be appreciated by those skilled in the art, the peptides either isolated by the aforementioned procedures or chemically synthesized or recombinantly produced can be reconstituted with a variety of purified natural or recombinant stress proteins in vitro to generate immunogenic noncovalent stress protein-antigenic molecule complexes. Alternatively, exogenous antigens or antigenic/immunogenic fragments or derivatives thereof can be noncovalently complexed to stress proteins for use in the immunotherapeutic or prophylactic vaccines of the invention. A preferred, exemplary protocol for noncovalently complexing a stress protein and an antigenic molecule in vitro is discussed below.

Prior to complexing, the hsps are pretreated with ATP or low pH to remove any peptides that may be associated with the hsp of interest. When the ATP procedure is used, excess ATP is removed from the preparation by the addition of apyranase as described by Levy, et al., 1991, *Cell* 67:265–274. When the low pH procedure is used, the buffer is readjusted to neutral pH by the addition of pH modifying reagents.

The antigenic molecules (1 μg) and the pretreated hsp (9 μg) are admixed to give an approximately 5 antigenic molecule: 1 stress protein molar ratio. Then, the mixture is incubated for 15 minutes to 3 hours at 4° to 45° C. in a suitable binding buffer such as one containing 20 mM sodium phosphate, pH 7.2, 350 mM NaCl, 3 mM MgCl$_2$ and 1 mM phenyl methyl sulfonyl fluoride (PMSF). The preparations are centrifuged through a Centricon® 10 assembly (Millipore) to remove any unbound peptide. The association of the peptides with the stress proteins can be assayed by SDS-PAGE. This is the preferred method for in vitro complexing of peptides isolated from MHC-peptide complexes of peptides disassociated from endogenous hsp-peptide complexes.

In an alternative embodiment of the invention, preferred for producing complexes of hsp70 to exogenous antigenic molecules such as peptides, 5–10 micrograms of purified hsp is incubated with equimolar quantities of the antigenic molecule in 20 mM sodium phosphate buffer pH 7.5, 0.5 M NaCl, 3 mM MgCl$_2$ and 1 mM ADP in a volume of 100 microliter at 37° C. for 1 hr. This incubation mixture is further diluted to 1 ml in phosphate-buffered saline.

In an alternative embodiment of the invention, preferred for producing complexes of hsp90 to peptides, 5–10 micrograms of purified hsp90 is incubated with equimolar or excess quantities of the antigenic peptide in a suitable buffer such as one containing 20 mM sodium phosphate buffer pH 7.5, 0.5M NaCl, 3 nM MgCl$_2$ at 60–65° C. for 5–20 min. Alternatively, equimolar or excess quantities of peptide (e.g., exogenous peptide) are added to purified hsp90-peptide (endogenous) complex, such that the exogenous peptide is exchanged for the endogenous peptide. In either case, the incubation mixture is allowed to cool to room temperature and centrifuged one or more times if necessary, through a Centricon® 10 assembly (Millipore) to remove any unbound peptide.

In an alternative embodiment of the invention, preferred for producing complexes of gp96 to peptides, 100–300 nM purified peptide is added to 100 nM purified gp96. Alternatively, 100–300 nM peptide (e.g., exogenous peptide) is added to purified gp96-peptide (endogenous) complex, such that the exogenous peptide is exchanged for the endogenous peptide. In either case, the mixture is incubated in a binding buffer consisting of 20 mM HEPES, pH 7.2, 20 mM NaCl, and 2 mM MgCl$_2$ at 60° C. for 10 min. and allowed to cool to room temperature for an additional 10 min. After centrifugation, the sample is incubated for 30 min. at room temperature. Free peptide is removed completely using a microcon 50 (Amicon, Inc.).

Once complexes have been isolated, they can be characterized further for tolerogenicity in animal models using the preferred administration protocols and excipients discussed below.

5.3. Dosage Regimens

Hsps and hsp-antigenic molecule complexes are administered to mammalian subjects, e.g., primates, dogs, cats, mice, rats, horses, cows, pigs, etc., preferably humans, in doses in a range of about 5 μg to about 5000 μg, preferably in a range of about 5 μg to about 1500 μg. In mammals, a range of about 50 μg to about 500 μg, either intradermally or subcutaneously is more preferred, with about 50 μg to about 200 μg subcutaneously and about 5 μg to about 100 μg intradermally even more preferred. Thus, while both subcutaneous and intradermal routes of administration are effective, intradermal injections typically require a lower dosage and are, therefore, preferred with respect to economy of materials. As demonstrated in the example in Section 6, below, an effective dose for treatment of IDDM in the NOD mouse model is 100 μg gp96 subcutaneously or 10 μg gp96 intradermally for mice of average mass of 20–25 g.

Methods of introduction include but are not limited to intradermal, intramuscular, intraperitoneal, intravenous, subcutaneous, intranasal, epidural, and oral routes. The hsps or complexes may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local; this may be achieved, for example and not by way of limitation, by topical application, by injection, by means of a catheter, by means of a suppository, or by means of an implant, said implant being of a porous, non-porous, or gelatinous material, including membranes, such as sialastic membranes, or fibers.

In a specific embodiment, the hsp compositions are administered, either intradermally or subcutaneously, with sites of administration varied sequentially. For example, and not by way of limitation, the doses recited above are given once weekly for a period of about 4 to 6 weeks, and the mode of administration is varied with each administration. Each site of administration may be varied sequentially. Thus, by way of example and not limitation, the first injection can be given, either intradermally or subcutaneously, on the left arm, the second on the right arm, the third on the left belly, the fourth on the right belly, the fifth on the left thigh, the sixth on the right thigh, etc. The same site can be repeated after a gap of one or more injections. Also, split injections can be given. Thus, for example, half the dose can be given in one site and the other half in another site on the same day.

After 4–6 weeks, further injections are preferably given at two-week intervals over a period of time of one month. Later injections can be given monthly. The pace of later injections can be modified, depending upon the patient's clinical progress and responsiveness to the immunotherapy. Alternatively, the mode of administration is sequentially varied, e.g., weekly administrations are given in sequence intradermally or subcutaneously.

5.4. Formulation

The uncomplexed hsps or hsps complexed with antigenic molecules, in accordance with the invention, can be formulated into pharmaceutical preparations for administration to mammals, preferably humans, for treatment or prevention of autoimmune diseases. Compositions comprising a compound of the invention formulated in a compatible pharmaceutical carrier can be prepared, packaged, and labelled for treatment of the autoimmune disease, such as insulin dependent diabetes mellitus, multiple sclerosis, systemic lupus erythematosus, Sjogren's syndrome, scleroderma, polymyositis, chronic active hepatitis, mixed connective tissue disease, primary biliary cirrhosis, pernicious anemia, autoimmune thyroiditis, idiopathic Addison's disease, vitiligo, gluten-sensitive enteropathy, Graves' disease, myasthenia gravis, autoimmune neutropenia, idiopathic thrombocytopenia purpura, rheumatoid arthritis, cirrhosis, pemphigus vulgaris, autoimmune infertility, Goodpasture's disease, bullous pemphigoid, discoid lupus, or dense deposit disease.

If the complex is water-soluble, then it can be formulated in an appropriate buffer, for example, phosphate buffered saline or other physiologically compatible solutions. Alternatively, if the resulting complex has poor solubility in aqueous solvents, then it can be formulated with a non-ionic surfactant such as Tween, or polyethylene glycol. Thus, the compounds and their physiologically acceptable solvates can be formulated for administration by inhalation or insufflation (either through the mouth or the nose) or oral, buccal, parenteral, rectal administration.

For oral administration, the pharmaceutical preparation can be in liquid form, for example, solutions, syrups or suspensions, or can be presented as a drug product for reconstitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions can take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well-known in the art.

Preparations for oral administration can be suitably formulated to give controlled release of the active compound.

For buccal administration, the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

The compositions can, if desired, be presented in a pack or dispenser device which can contain one or more unit dosage forms containing the active ingredient. The pack can for example comprise metal or plastic foil, such as a blister pack. The pack or dispenser device can be accompanied by instructions for administration.

The invention also provides kits for carrying out the therapeutic regimens of the invention. Such kits comprise in one or more containers therapeutically or prophylactically effective amounts of the hsp or hsp-antigenic molecule complexes in pharmaceutically acceptable form. The hsp or hsp-antigenic molecule complex in a vial of a kit of the invention can be in the form of a pharmaceutically acceptable solution, e.g., in combination with sterile saline, dextrose solution, or buffered solution, or other pharmaceutically acceptable sterile fluid. Alternatively, the complex can be lyophilized or desiccated; in this instance, the kit optionally further comprises in a container a pharmaceutically acceptable solution (e.g., saline, dextrose solution, etc.), preferably sterile, to reconstitute the complex to form a solution for injection purposes.

In another embodiment, a kit of the invention further comprises a needle or syringe, preferably packaged in sterile form, for injecting the complex, and/or a packaged alcohol pad. Instructions are optionally included for administration of hsp or hsp-antigenic molecule complexes by a clinician or by the patient.

5.5. Treatment of Autoimmune Disease

The compositions and formulations described above in Sections 5.2 and 5.4 can be used to treat autoimmune disease, including, but are not limited to, insulin dependent diabetes mellitus, multiple sclerosis, systemic lupus erythematosus, Sjogren's syndrome, scleroderma, polymyositis, chronic active hepatitis, mixed connective tissue disease, primary biliary cirrhosis, pernicious anemia, autoimmune thyroiditis, idiopathic Addison's disease, vitiligo, gluten-sensitive enteropathy, Graves' disease, myasthenia gravis, autoimmune neutropenia, idiopathic thrombocytopenia purpura, rheumatoid arthritis, cirrhosis, pemphigus vulgaris, autoimmune infertility, Goodpasture's disease, bullous pemphigoid, discoid lupus, ulcerative colitis, and dense deposit disease. Administration of hsp-based compositions can be used to effect tolerance of self tissues and organs that are targets of autoimmune responses, or of tissues transplanted to replace such self target tissues and organs.

5.5.1. Methods of Treatment Based on Administration of Hsps

For treatment of IDDM, the hsps administered in accordance with the invention are most effective in NOD mice hen administered just prior to the onset of glycosuria. hen the age of onset of glycosuria cannot be predicted, as is typical with human patients, hsps are preferably administered prior to the onset of islet cell damage once mild glycosuria and mild to moderate levels of hyperglycemia are observed. When administered at this stage, they should provide long term protection against autoimmune disease. Therefore, the methods of treatment of the invention are therapeutic; they protect against the autoimmune response after it has developed. While administration prior to autoimmune response (prophylaxis) is provided by the invention, it is not required and is not as effective as post-response administration.

The example presented in Section 6, below, details the use in accordance with the methods of the invention of the hsp gp96 in immunotherapy in an experimental autoimmune disease model for insulin dependent diabetes mellitus (IDDM). The example presented in Section 7, below, details the use in accordance with the methods of the invention of hsp in immunotherapy in humans for IDDM.

Transplantation is a common form of treatment of autoimmune disease, especially when the target self tissue has been severely damaged. For example, and not by way of limitation, pancreas transplantation and islet cell transplantation are common treatment options for IDDM (See, e.g., Brunicardi, 1996, Transplant. Proc. 28: 2138–40; Kendall & Robertson, 1996, Diabetes Metab. 22: 157–163; Hamano et al., 1996, Kobe J. Med. Sci. 42: 93–104; Larsen & Stratta, 1996, Diabetes Metab. 22: 139–146; and Kinkhabwala, et al., 1996, Am. J. Surg. 171: 516–520). As with any transplantation method, transplantation therapies for autoimmune disease patients include treatments to minimize the risk of host rejection of the transplanted tissue. However, autoimmune disease involves the additional, independent risk that the pre-existing host autoimmune response which damaged the original self tissue will exert the same damaging effect on the transplanted tissue. Accordingly, the present invention encompasses methods and compositions for the treatment of autoimmune disease using heat shock proteins in individuals undergoing transplantation therapy of the autoimmune disease.

In accordance with the invention, the hsp-based compositions and formulations described in Sections 5.2 and 5.4, above, are administered to prevent and treat damage to the transplanted organ, tissue, or cells resulting from the host individual's autoimmune response initially directed against the original self tissue. Preferably, administration is carried out both prior and subsequent to transplantation in 2 to 4 doses each one week apart, at least one of which precedes the transplantation.

5.6. Monitoring of Effects During Autoimmune Disease Immunotherapy

The effects/efficacy of treatment of autoimmune disease according to the present invention can be detected, for example, on the level of the molecular and cellular agents involved in the immune response (e.g., cytotoxic T cells), or on the level of an affected tissue, or on the level of secondary symptoms. In IDDM, one such secondary symptom, glycosuria (i.e., excess sugar in the urine), can be readily assayed to provide an index of the disease state. Accordingly, excess urine in a patient sample as compared with a normal patient sample is symptomatic of IDDM. Efficacy of treatment of such a patient having IDDM is indicated by a resulting decrease in the amount of excess glucose in the urine. In a preferred embodiment for IDDM monitoring, urine samples from patients are assayed for the presence of glucose using techniques well known in the art. Glycosuria in humans is defined by a urinary glucose concentration exceeding 100 mg per 100 ml. Excess sugar levels in those patients exhibiting glycosuria can be measured even more precisely by obtaining blood samples and assaying serum glucose.

6. EXAMPLE: ADMINISTRATION OF GP96 TO AUTOIMMUNE DIABETES MODELS IN MICE

The results described below demonstrate, for the first time, the regulatory function of the hsp gp96 as an inducer of antigen-specific immune suppression. Gp96 vaccination of pre-diabetic Non Obese Diabetic (NOD) mice can elicit long-term protection from diabetes. High doses of hsps, in the presence of an activated T cell population, lead to the production of suppressor population which specifically acts upon the activated T cells. Furthermore, the results below demonstrate that the suppressor cell population elicits protection from autoimmune damage that is long term and can be adoptively transferred.

These results demonstrate that hsps administered in accordance with the invention are ideal interventional agents against autoimmunity. Specifically, such administered hsps 1) trigger protective immunoregulatory mechanisms effective when administered after the onset of autoimmune damage and, therefore, are immunotherapeutic, as opposed to prophylactic; 2) are effective for long-term protection; 3) effect antigen-specific immune suppression via antigen presenting cells (APCs) which trigger production of suppressor CD4+ cells that inactivate autoreactive T cells; 4) have a more general effect than individual administered autoantigens, and thus do not require identification of individual autoantigens for effectiveness; 5) nonetheless, have an effect that is specific to at least a substantial portion of the autoantigens that activate autoreactive T cells; 6) are less physiologically disruptive than such non-specific agents as cytokines, because the effect of hsps on the cytokine milieu is mediated through the endogenous, local, cellular response instead of systemically; 7) are of mammalian origin; and 8) are adjuvant free.

These results indicate that administration of hsps in accordance with the methods described below are a novel immunotherapeutic modality, ideal for the treatment of autoimmune diabetes and other autoimmune diseases as well.

6.1. Materials and Methods

6.1.1. Mice

In vivo assays of efficacy of the immunization regimens were assessed in female NOD/LtJ mice (commercially available from The Jackson Laboratory, Bar Harbor, Me.). Incidence rates of diabetes in these mice were consistent with those reported in literature, wherein over 80% of female mice developed diabetes by 24 weeks of age and onset of insulitis commenced between 6–8 weeks age. NOD mice are inbred and highly responsive to a variety of immunoregulatory strategies. Adult NOD mice (6–8 weeks of age) have an average mass of 20–25 g.

6.1.2. Gp96 purification

Tissue (liver or pancreas) was obtained from C57/B6 mice (Jackson Laboratory, Bar Harbor, Me.) and processed for purification of hsp-peptide complexes as described earlier (Srivastava et al., 1986, Proc. Natl. Acad. Sci. USA 83: 3407–3411). In all experiments, gp96 was prepared as a complex with endogenous peptide.

6.1.3. Immunization

Gp96-peptide complexes were quantified using spectrometric analysis and appropriate protein quantities were resuspended prior to injection in 50 µl phosphate buffered saline (PBS) per dose. Two injections, one week apart, were administered subcutaneously under the dorsal skin of each mouse.

6.1.4. Monitoring

Monitoring was performed on two separate occasions prior to immunization and performed weekly throughout the treatment and continued thereafter. Urine was tested for glucose every eek (Keto-Diastix®; Miles Inc., Kankakee, Ill.) and glycosuric mice were checked for serum glucose (ExacTech®, MediSense, Inc., Waltham, Mass.). Diabetes was diagnosed when fasting glycemia was greater than 2.5g/L.

6.1.5. Adoptive Transfer of Splenic White Cells

Splenic white blood cells were obtained from mice that had been vaccinated intradermally with gp96-peptide complexes at least 5 months prior to their sacrifice and were protected from diabetes in the entire post-immunization period. $5 \times 10^7$ splenic white cells obtained from either pre-immunized NOD mice or protected NOD mice were suspended in $500$ µl PBS and were injected intravenously, retro-orbitally into a fresh batch of 6–8 week-old NOD mice. Similar quantities of cells obtained from non-diabetic NOD mice were injected as controls.

6.1.6. Adoptive Transfer of Fractionated CD4+ and CD8+ Splenic T Cells

Donor NOD mice treated intradermally with 10 µg gp96 complexed with endogenous peptide were parked (i.e., held without further treatment) for 8 weeks and shown to be protected from diabetes. Prediabetic mice, the same age as the recipients, were used as control donors.

Donor mice were sacrificed and their spleen cells were harvested. Red blood cells were removed by lysis by incubating the cell mixture in a filtered solution containing 0.14M ammonium chloride and 0.17M Tris-HCl, pH 7.2. The residual cells were treated with magnetic activated cell sorter (MACS) antibodies reactive with CD4+ and CD8+ cells and loaded onto MACS VS+ Separation Column (Miltenyi Biotec GmbH, Germany). The column containing bound CD4+ and CD8+ cells was washed several times. The cells were eluted off the column by washing the column after removal from the magnetic source and counted. The purity of the CD4+ cells (82% protected mice, 71% control mice) and CD8+ cells (92% protected mice, 67% control mice) was confirmed using fluorescent activated cell sorter (FACS) analysis using a FACScan with Cellquest software (Becton Dickenson, San Jose, Calif.). Cells were resuspended in RPMI-1640 prior to intravenous injection.

Recipient NOD mice were 6–8 weeks old and confirmed non-diabetic at the time of transfer. Untreated recipients or recipients that had received buffer intravenously were used as controls for comparing the degree of protection offered by the adoptive transfer.

Cells were suspended in 200 µl volume of plain RPMI and injected intravenously via the retro-orbital venous plexus. Cell numbers transferred were: 7.5 million CD4+ alone; 4 million CD8+ alone; and 7.5 million CD4+ combined with 4 million CD8+. The cell numbers injected were kept constant irrespective of whether obtained from the treated or the untreated groups of donors.

6.2. Results

In all experiments, each gp96 sample was obtained and used as a complex with endogenous peptide. NOD mice (obtained at 6–8 weeks of age) were immunized at the age of 8 weeks using hsps obtained from sources and in the doses specified: Liver-derived gp96, and pancreas-derived gp96, each in doses of 100 µg (FIG. 1A), 25 µg (FIG. 1B), and 10 µg (FIG. 1C) for each group of five animals. Immunization schedules were as described in Section 6.1.3, above. Control animals were either immunized with PBS-buffer, or were left untreated. As shown in FIGS. 1A–C, gp96-induces long term protection against spontaneous diabetes. Immunization with gp96-peptide complexes derived from mouse liver or pancreas at a dose of 100 µg administered subcutaneously can prevent the spontaneous induction of diabetes in 80% of NOD mice for as long as 8 months as compared to no protection in the untreated group. There is a dose-related response, wherein, lower doses (10 µg subcutaneous) neither delay the onset nor provide protection, intermediate doses (25 µg subcutaneous) delay the onset but do not provide protection, and higher doses (100 µg subcutaneous) provide permanent protection. Lower doses do not hasten the onset of diabetes. Moreover, there was no observed induction or exacerbation of IDDM symptoms in any of the animals as a consequence of gp96 administration.

Unexpectedly, however, there does not appear to be any organ specificity requirement for the source of the gp96: gp96-peptide complexes derived from either liver or pancreas offers protection from diabetes. Furthermore, adjuvant was not used and is, therefore, not required.

In order to determine the specificity of the role of gp96 with respect to other proteins in providing protection, animals immunized with gp96-peptide complexes were compared to control animals immunized with either (i) PBS buffer; (ii) chicken egg albumin (ovalbumin), equivalent of 45 µg/dose; (iii) beta-galactosidase, equivalent of 100 µg/dose; or (iv) phosphorylase-b, equivalent of 100 µg/dose (FIGS. 2A–B). Both, ovalbumin and beta-galactosidase were suspended in PBS and only the supernatant of a post-100,000×g centrifugation was used. This step ensured that only soluble fractions of these proteins were tested, as gp96 is a soluble protein. Mice immunized with the control proteins were unprotected against diabetes and found to develop diabetes at rates comparable to those left untreated.

Therapy of NOD mice 5 weeks of age, using similar doses described above for the 8 week old NOD mice, was also tested. Results indicated that commencement of therapy with gp96-peptide complexes when the mice were 5 weeks old was not as effective as commencement at around 8 weeks of age (FIGS. 3A–B). Vaccination too early (5 weeks) provided less protection from diabetes. This result indicates that gp96 mediated suppression depends on the combined prior appearance of autoantigen(s) and activated T cells reactive against the autoantigen(s).

In order to assess whether protection from diabetes was adoptively transferrable, the following experiment was performed. NOD mice were treated at the age of 8 weeks with liver-derived gp96-peptide complexes or pancreatic-gp96-peptide complexes, each complex in doses of 100 µg per group of animals. All animals were monitored and found free of diabetes for six months following their immunotherapy. Splenic white cells obtained from these animals were adoptively transferred into a fresh batch of 8-week old NOD mice which were normogylcemic at the time of the transfer. Results indicated that adoptive transfer of $5 \times 10^7$ splenic white cells/dose given in two doses can protect untreated NOD mice from diabetes, whereas control (pre-diabetic, untreated 6–8 week old NOD/LtJ mice) spleens cannot protect (FIG. 4).

In order to determine which type of T lymphocytes are responsible for the adoptive transfer of suppression of autoimmunity, donor NOD mice were protected from diabetes by treatment intradermally with 10 μg of gp96. Splenic cells were fractionated into CD4+ and CD8+ populations, which were then administered to recipient NOD mice either separately or in combination. As shown in FIGS. 5A–B, CD4+ cells obtained from protected mice transferred protection from diabetes (FIG. 5A), whereas controls did not provide protection (FIG. 5B). CD4+ cells alone were most effective, and CD4+ cells in combination with CD8+ cells, as well as whole spleen cells, also conferred protection. CD8+ cells alone did not confer protection.

These results demonstrate that immunization with hsp in accordance with the invention: 1) generates a T cell population that can suppress autoimmune damage; 2) is effective after the onset of insulitis and, therefore, therapeutic; 3) provides protection that can be adoptively transferred; and 4) provides long-term protection.

These results also indicate that gp96 immunotherapy in accordance with the invention is useful for treating diabetic patients undergoing islet cell transplantation. The grafted islet cells of transplant recipients are prone to the same autoreactive damage that originally destroyed the host cells (Verge, et al., 1996, Diabetes 45: 926–933; Tyden, et al., 1996, N. Engl. J. Med. 335: 860–863). Immune suppressors specific to only a single autoantigen would be unable to the suppress autoreactive processes directed to a new panoply of transplanted autoantigens for which the recipient suppressor T cell population was hitherto unprimed.

As mentioned above, gp96-mediated protection is most effective when therapy is commenced in mice around 8 weeks of age. Earlier vaccination (5 weeks) provides less effective protection from diabetes. Interestingly, the T-cell response to the autoantigen caused insulitis at around 6–8 weeks. These two events indicate that gp96 is effective in reversing T-cell-mediated beta cell damage, and that gp96 mediated suppression is closely linked to the presence of activated T cells. These results indicate that the optimal period for treatment of humans is at a correspondingly early stage in the development of diabetes, i.e., when mild to moderate glycosuria or hyper glycemia is observed.

Further experiments (data not shown) demonstrated that antigen presenting cells (APCs), upon exposure to hsps, release cytokines such as IFN, and IL-12.

Although the inventors are not required to provide an explanation of the underlying mechanism by which tolerance is effected by the present invention, and without intending to be bound by any one particular mechanistic theory, the following discussion is provided regarding believed mechanisms of the invention. As explained above, gp96-mediated suppression of the pathological immune attack against pancreas cells was not dependent on the source of the gp96 —liver derived gp96, as well as pancreas derived gp96, provided protection. However, the gp96-mediated suppression appears to be dependent on the pre-existing development of the beta-cell-specific autoimmune attack. Thus, the source of gp96 does not require tissue specificity in order to effect suppression because its suppressive activity is only effective against a previously activated T cell response, which is specific. In other words, gp96 suppressive activity is general and, therefore, is not effective, until activated target T cells (which are specifically attacking a self autoantigen) are present, at which time gp96 can suppress that autoimmune T cell activity. Upon exposure to hsps, APCs overproduce a cytokine that activates a regulatory T cell (Tr). When exposed to an activated autoreactive CD8+ T cell (CTL), Tr is transformed into a suppressor T cell (Ts) which inactivates the CTL, effecting protection.

7. EXAMPLE: IMMUNOTHERAPY OF HUMAN IDDM PATIENTS

Immunotherapy is initiated at an early stage in the development of IDDM, preferably when mild glycosuria and/or mild to moderate hyperglycemia are observed. Patients are injected with hsps, either uncomplexed or complexed with peptide, derived from any tissue source, whether autologous, allogeneic, or recombinant. The therapeutic regimen of hsp, for example, gp96, hsp90, hsp70, or a combination thereof, or hsp-peptide complexes containing these hsps, includes weekly injections of the hsp or hsp-peptide complex, dissolved in saline or other physiologically compatible solution. The dosage used is in the range of about 5 μg to about 1500 μg hsp, administered either intradermally or subcutaneously.

The first four to six injections are given at weekly intervals. Subsequently, two injections are given at two-week intervals; followed by a regimen of injections at monthly intervals. The effect of hsp or hsp-peptide complexes therapy is monitored by measuring the amount of glucose present in the urine, or, alternatively, in the serum. Patients suffering from IDDM have excess levels of blood glucose, e.g., 140 mg per 100 ml. Effective treatment is indicated by a reduction in urinary glucose levels toward normal levels, e.g., less than 100 mg per 100 ml.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method of treating autoimmune disease in a mammal comprising administering to the mammal a composition comprising a purified population of complexes consisting essentially of heat shock protein noncovalently bound to a peptide, wherein the heat shock protein is a member of the hsp90 family.

2. The method of claim 1, wherein the heat shock protein is not an autoantigen of said autoimmune disease.

3. The method of claim 1, wherein the peptide is not an autoantigen of said autoimmune disease.

4. A method of treating an autoimmune disease in a mammal comprising administering to the mammal a composition comprising a purified heat shock protein which is substantially free of complexed peptide, wherein the heat shock protein is a member of the hsp90 family.

5. The method of claim 4, wherein the heat shock protein is not an autoantigen of said autoimmune disease.

6. A method of treating autoimmune disease in a mammal comprising administering to the mammal a composition comprising a purified population of complexes consisting essentially of heat shock protein noncovalently bound to a peptide, wherein the heat shock protein is a member of the hsp70 family.

7. The method of claim 6, wherein the heat shock protein is not an autoantigen of said autoimmune disease.

8. The method of claim 6, wherein the peptide is not an autoantigen of said autoimmune disease.

9. A method of treating an autoimmune disease in a mammal comprising administering to the mammal a composition comprising a purified heat shock protein which is substantially free of complexed peptide, wherein the heat shock protein is a member of the hsp70 family.

10. The method of claim 6, wherein the heat shock protein is not an autoantigen of said autoimmune disease.

11. The method of claim 1, 4, 2, 3, or 5, wherein the mammal is human.

12. The method of claim 11 wherein the autoimmune disease is insulin dependent diabetes mellitus, multiple sclerosis, systemic lupus erythematosus, Sjogren's syndrome, scleroderma, polymyositis, chronic active hepatitis, mixed connective tissue disease, primary biliary cirrhosis, pernicious anemia, autoimmune thyroiditis, idiopathic Addison's disease, vitiligo, gluten-sensitive enteropathy, Graves' disease, myasthenia gravis, autoimmune neutropenia, idiopathic thrombocytopenia purpura, rheumatoid arthritis, cirrhosis, pemphigus vulgaris, autoimmune infertility, Goodpasture's disease, bullous pemphigoid, discoid lupus, ulcerative colitis, or dense deposit disease.

13. The method of claim 1, 4, 2, 3, or 5, wherein the autoimmune disease is insulin dependent diabetes mellitus.

14. The method of claim 13 wherein the heat shock protein is gp96.

15. The method of claim 14 wherein the amount of the heat shock protein present in the composition is in a range of 5 $\mu$g to 5000 $\mu$g.

16. The method of claim 14 wherein the amount of the heat shock protein present in the composition is in a range of 5 $\mu$g to 1500 $\mu$g.

17. The method of claim 14 wherein the amount of the heat shock protein present in the composition is in a range of 50 $\mu$g to 500 $\mu$g.

18. The method of claim 14 wherein the amount of the heat shock protein present in the composition is in a range of 50 $\mu$g to 200 $\mu$g.

19. The method of claim 18 wherein the composition is administered subcutaneously.

20. The method of claim 14 wherein the amount of the heat shock protein present in the composition is in a range of 5 $\mu$g to 100 $\mu$g.

21. The method of claim 20 wherein the composition is administered intradermally.

22. The method of claim 1, 4, 2, 3, or 5, further comprising transplanting cells, tissue, or an organ, which correspond to the cells, tissue, or organ affected by the autoimmune disease, from a healthy donor to the mammal being treated.

23. The method of claim 22 wherein the autoimmune disease is insulin dependent diabetes mellitus.

24. The method of claim 23 wherein the mammal is human.

25. The method of claim 23 wherein the heat shock protein is gp96.

26. The method of claim 23 wherein the heat shock protein is hsp90.

27. The method of claim 23 wherein the cells transplanted are pancreatic islet cells.

28. The method of claim 1, 4, 2, 3, or 5, wherein the heat shock protein is hsp90.

29. The method of claim 1, 4, 2, 3, or 5, wherein the disease is multiple sclerosis.

30. The method of claim 29, wherein the hsp is gp96.

31. The method of claim 6, 9, 7, 8, or 10 wherein the mammal is human.

32. The method of claim 31 wherein the autoimmune disease is insulin dependent diabetes mellitus, multiple sclerosis, systemic lupus erythematosus, Sjogren's syndrome, scleroderma, polymyositis, chronic active hepatitis, mixed connective tissue disease, primary biliary cirrhosis, pernicious anemia, autoimmune thyroiditis, idiopathic Addison's disease, vitiligo, gluten-sensitive enteropathy, Graves' disease, myasthenia gravis, autoimmune neutropenia, idiopathic thrombocytopenia purpura, rheumatoid arthritis, cirrhosis, pemphigus vulgaris, autoimmune infertility, Goodpasture's disease, bullous pemphigoid, discoid lupus, ulcerative colitis, or dense deposit disease.

33. The method of claim 6, 9, 7, 8, or 10, wherein the autoimmune disease is insulin dependent diabetes mellitus.

34. A method of treating autoimmune disease in a mammal comprising administering to the mammal a composition comprising a purified population of complexes consisting essentially of heat shock protein noncovalently bound to a peptide, wherein the heat shock protein is hsp70, hsp90, or gp96, or a combination of any of the foregoing.

35. The method of claim 32, wherein the peptide is not an autoantigen of said autoimmune disease.

36. The method of claim 34 wherein the mammal is human.

37. The method of claim 34 wherein the autoimmune disease is insulin dependent diabetes mellitus.

38. The method of claim 37 wherein the mammal is human.

39. A method of treating autoimmune disease in a mammal comprising administering to the mammal a composition comprising purified heat shock protein which is substantially free of complexed peptide, wherein the heat shock protein is hsp70, hsp90, or gp96, or a combination of any of the foregoing.

40. The method of claim 32 or 39, wherein the heat shock protein is not an autoantigen of said autoimmune disease.

* * * * *